(12) United States Patent
Hool

(10) Patent No.: US 11,801,380 B2
(45) Date of Patent: Oct. 31, 2023

(54) NON-INVASIVE NERVE STIMULATION DEVICES, ELECTRODE ASSEMBLIES, AND METHODS OF USE THEREOF

(71) Applicant: HOOLEST PERFORMANCE TECHNOLOGIES, INC., Phoenix, AZ (US)

(72) Inventor: Nicholas D. Hool, Phoenix, AZ (US)

(73) Assignee: HOOLEST PERFORMANCE TECHNOLOGIES, INC., Phoenix, AZ (US)

( * ) Notice: Subject to any disclaimer, the term of this patent is extended or adjusted under 35 U.S.C. 154(b) by 218 days.

(21) Appl. No.: 17/334,475

(22) Filed: May 28, 2021

(65) Prior Publication Data

US 2021/0290943 A1    Sep. 23, 2021

Related U.S. Application Data

(63) Continuation of application No. 17/050,618, filed as application No. PCT/US2019/029387 on Apr. 26, 2019, now Pat. No. 11,071,855.

(60) Provisional application No. 62/663,154, filed on Apr. 26, 2018, provisional application No. 62/663,186, filed on Apr. 26, 2018.

(51) Int. Cl.
*A61N 1/04* (2006.01)
*A61N 1/36* (2006.01)

(52) U.S. Cl.
CPC ......... *A61N 1/0456* (2013.01); *A61N 1/0484* (2013.01); *A61N 1/0496* (2013.01); *A61N 1/36025* (2013.01)

(58) Field of Classification Search
CPC .. A61N 1/0456; A61N 1/0484; A61N 1/0496; A61N 1/36025
See application file for complete search history.

(56) References Cited

U.S. PATENT DOCUMENTS

| 11,071,855 B2 * | 7/2021 | Hool .................... A61N 1/0456 |
| 2005/0165460 A1 | 7/2005 | Erfan |
| 2006/0122675 A1 | 6/2006 | Libbus et al. |
| 2011/0276112 A1 | 11/2011 | Simon et al. |
| 2015/0297889 A1 | 10/2015 | Simon et al. |
| 2017/0216593 A1 | 8/2017 | Lee |

FOREIGN PATENT DOCUMENTS

WO          2017173331 A1    5/2017

* cited by examiner

*Primary Examiner* — Alyssa M Alter
(74) *Attorney, Agent, or Firm* — Johnson, Marcou, Isaacs & Nix, LLC

(57) ABSTRACT

Nerve stimulation devices and methods for performing non-invasive nerve stimulation are provided that are particularly well suited for performing non-invasive stimulation of one or both of the great auricular nerve and auricular branch of the vagus nerve through a target nerve junction in the neck of the subject. The nerve stimulation devices use dry electrolyte electrodes that (1) are comfortable to use, (2) suitable for long-term use, (3) avoid delivering painful shocks to the subject, (4) do not require soaking of the electrodes in saline solutions or covering them in sticky or wet gels, (5) do not require skin preparation, and (6) avoid causing muscle contraction in areas outside of the target nerve junction containing the great auricular nerve and the auricular branch of the vagus nerve during use.

24 Claims, 25 Drawing Sheets

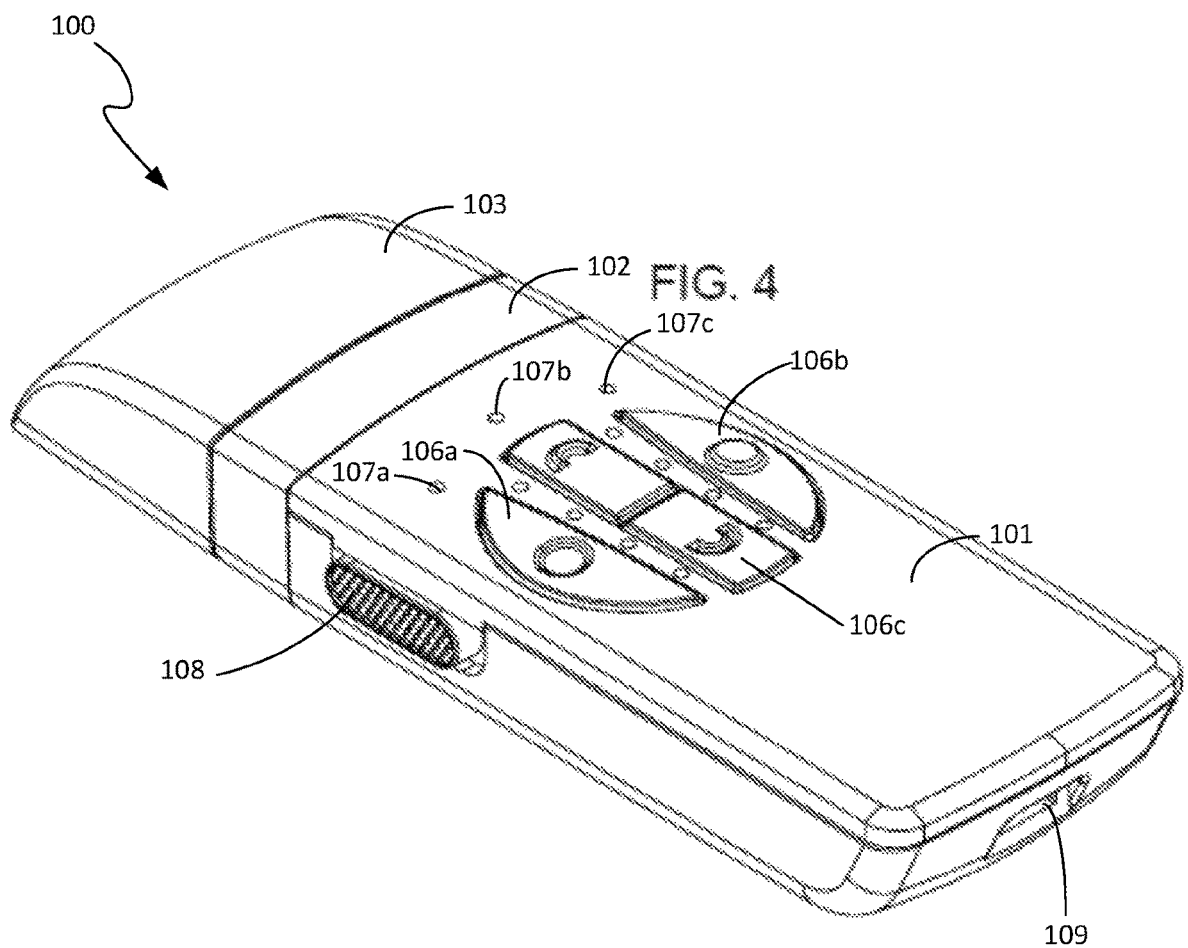
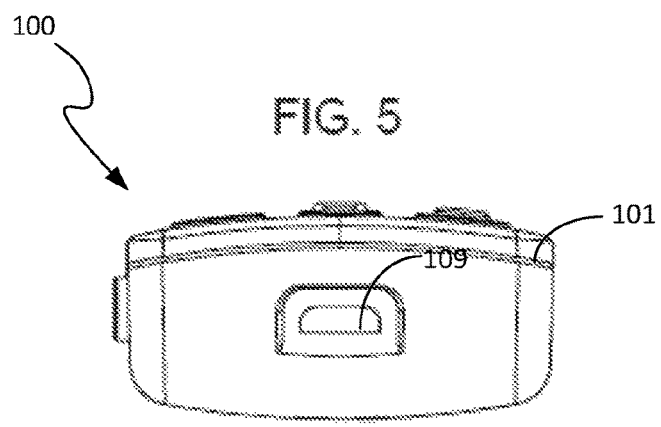

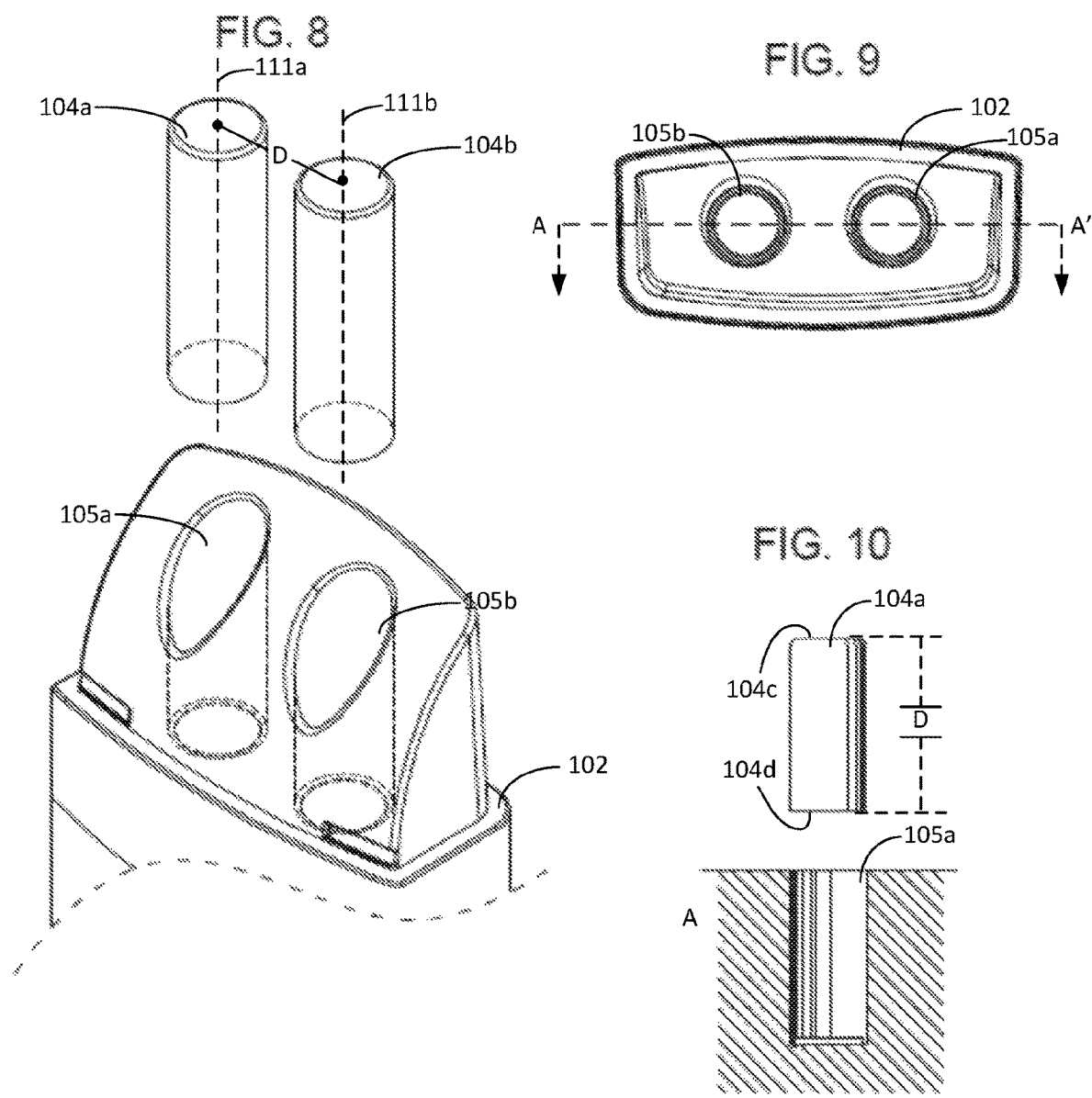

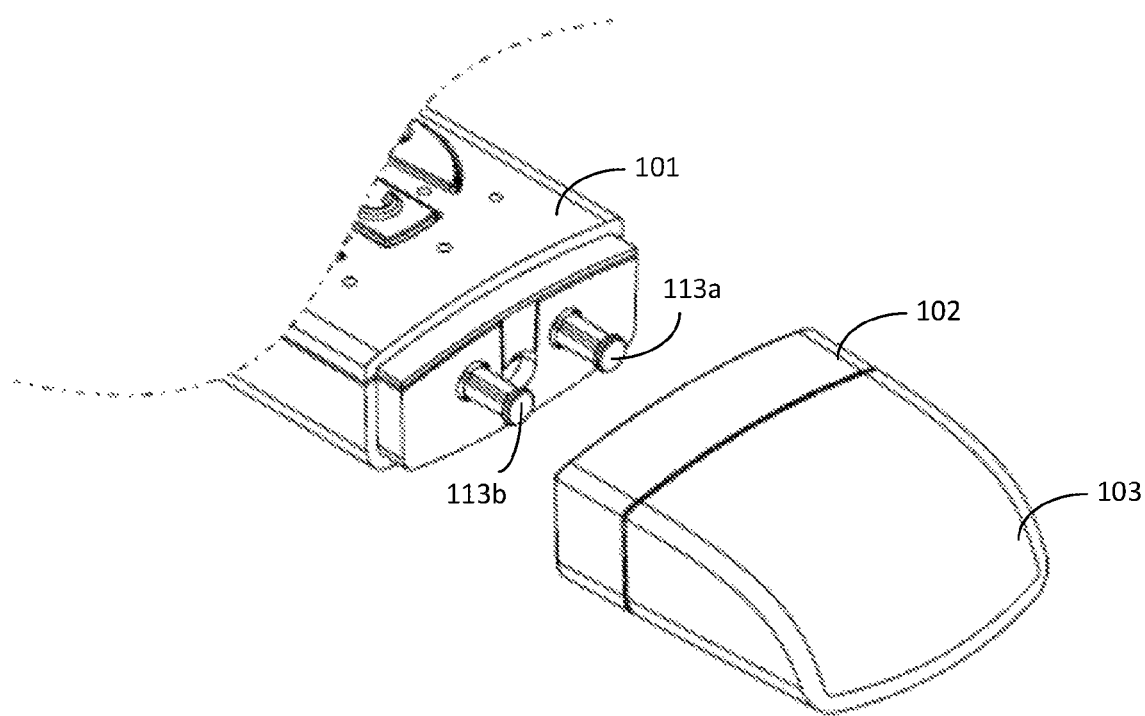
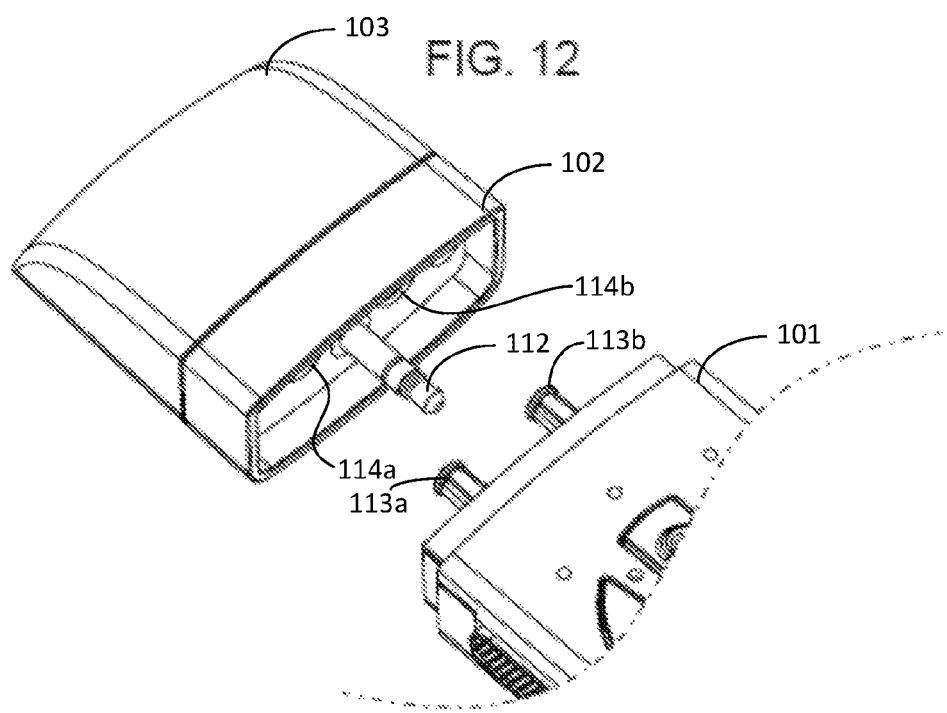

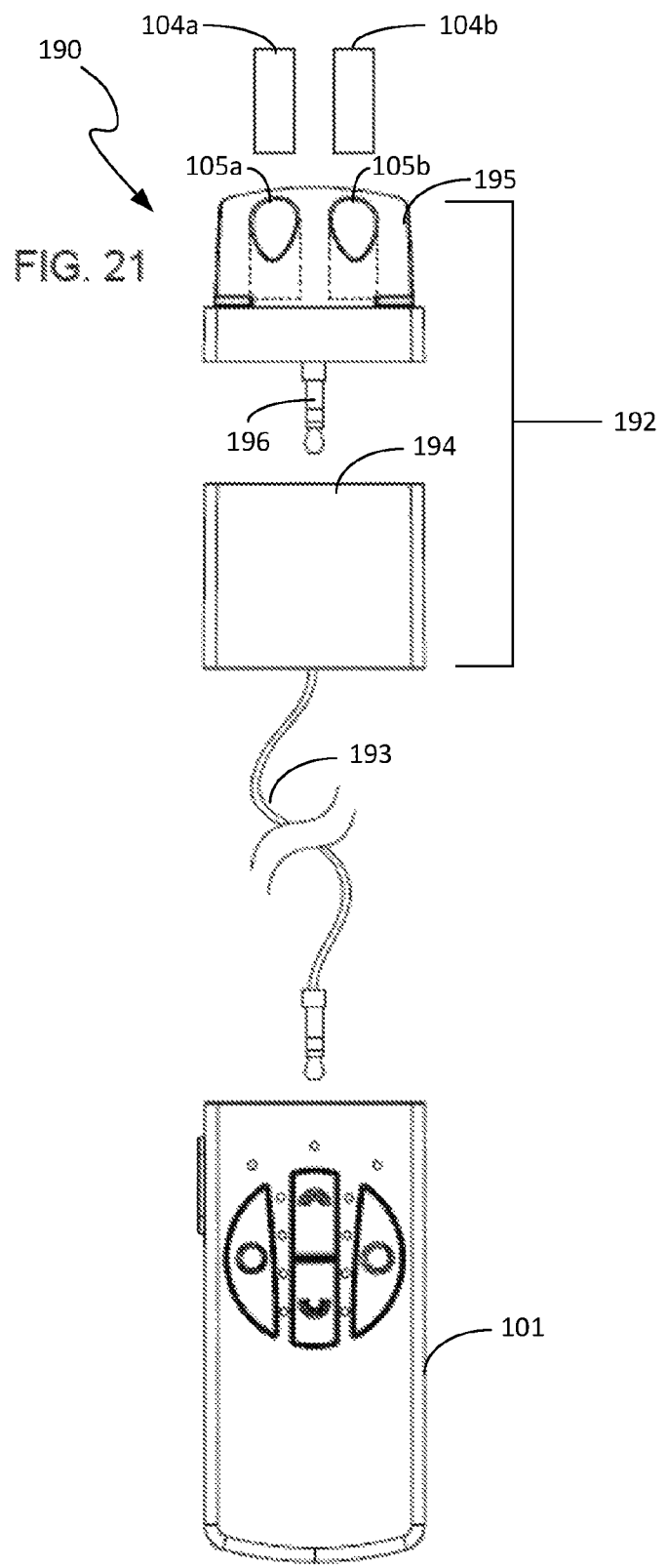

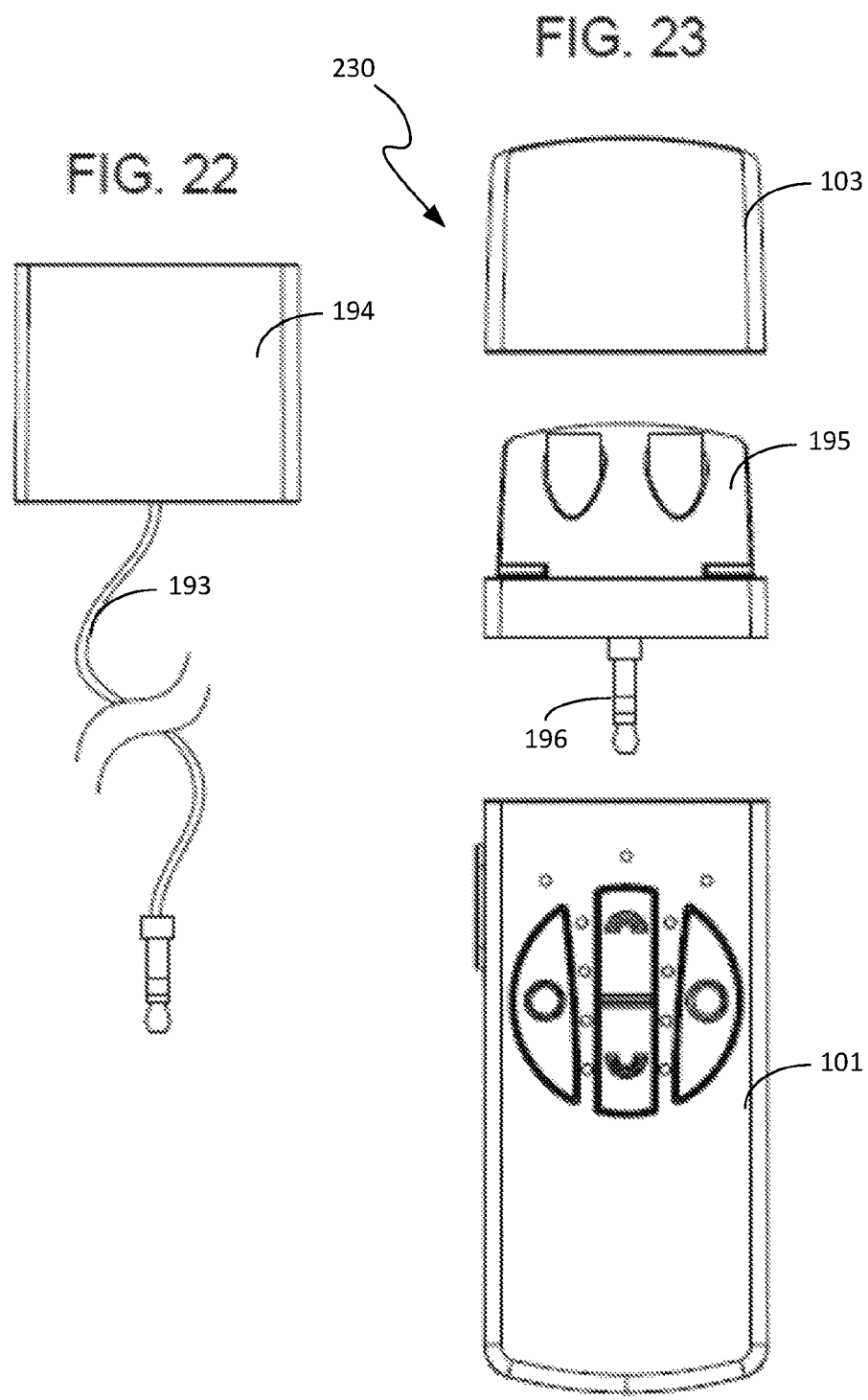

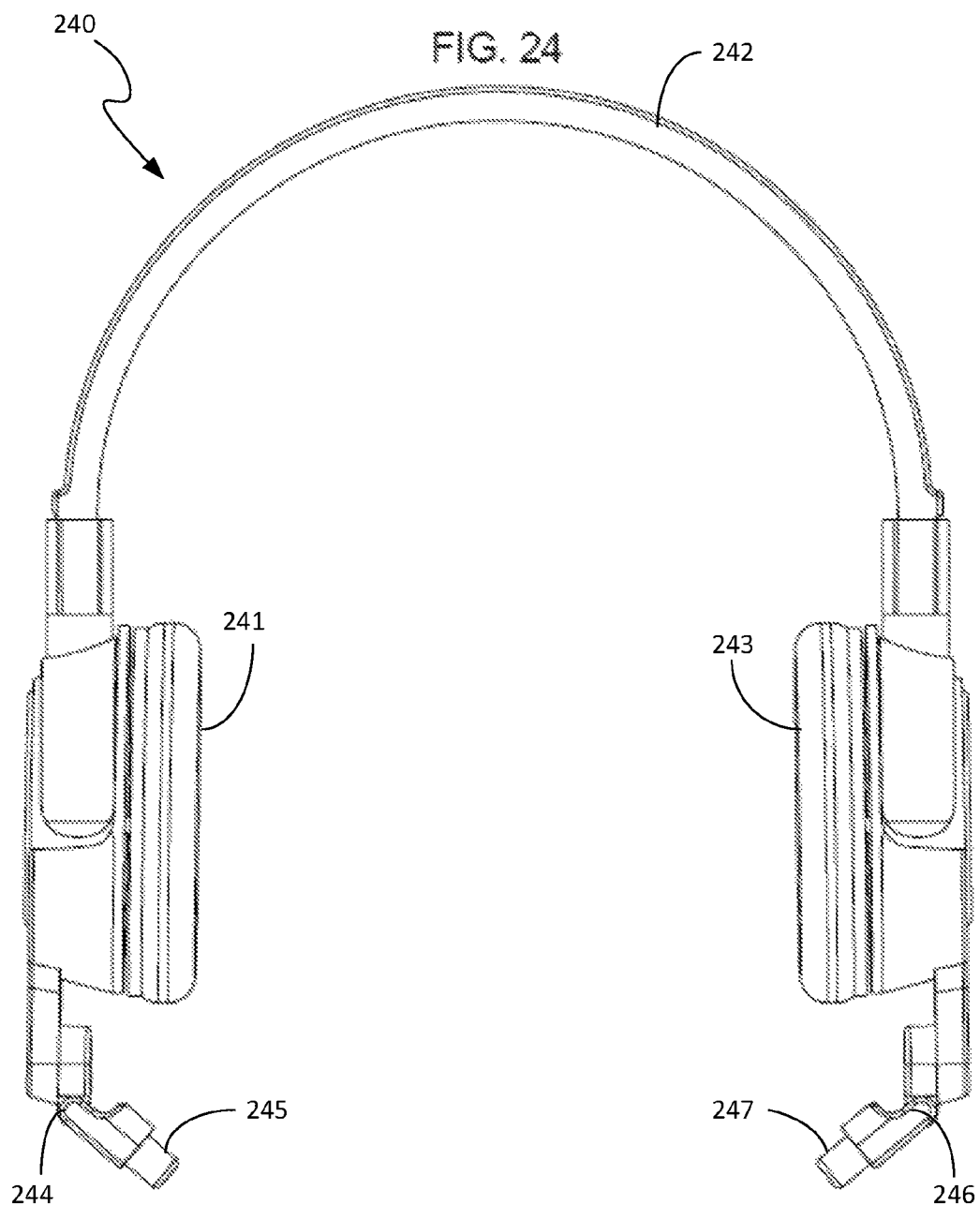

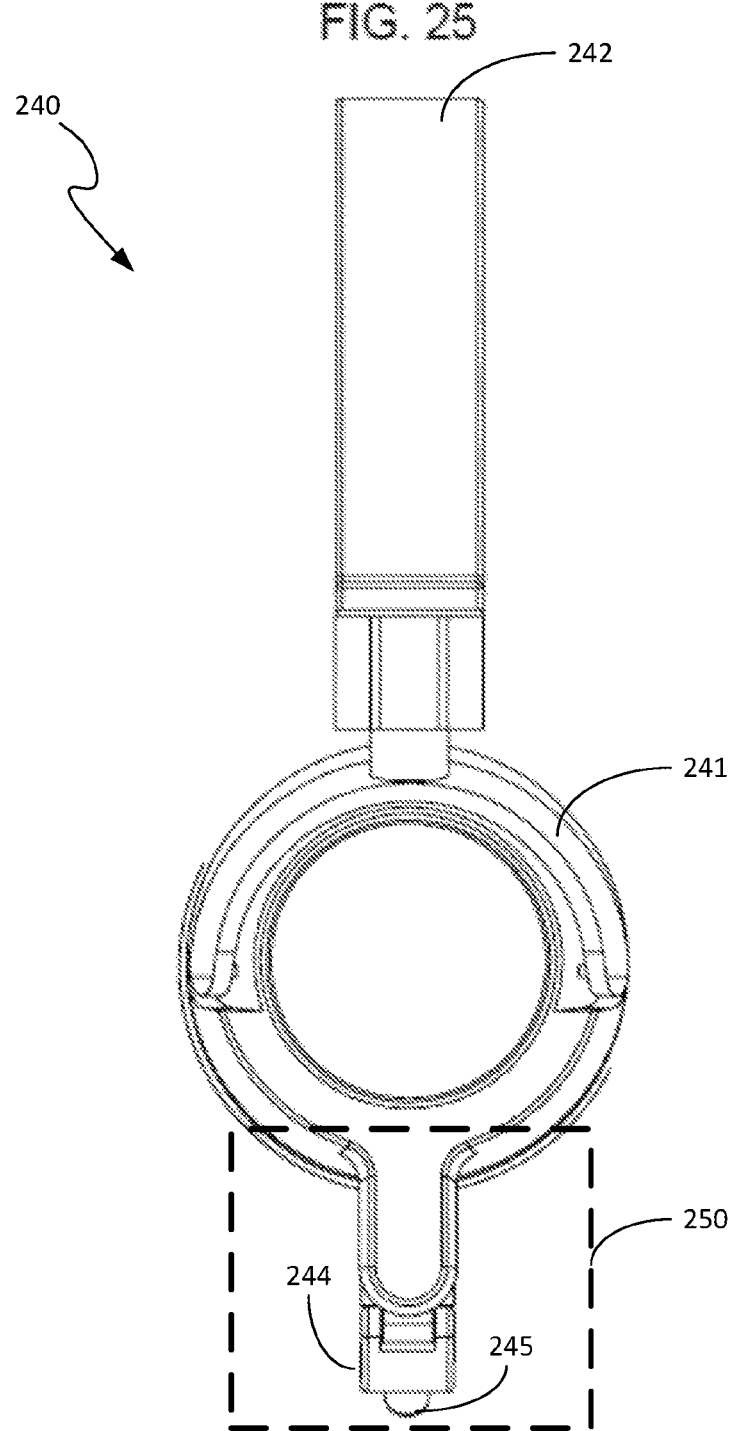

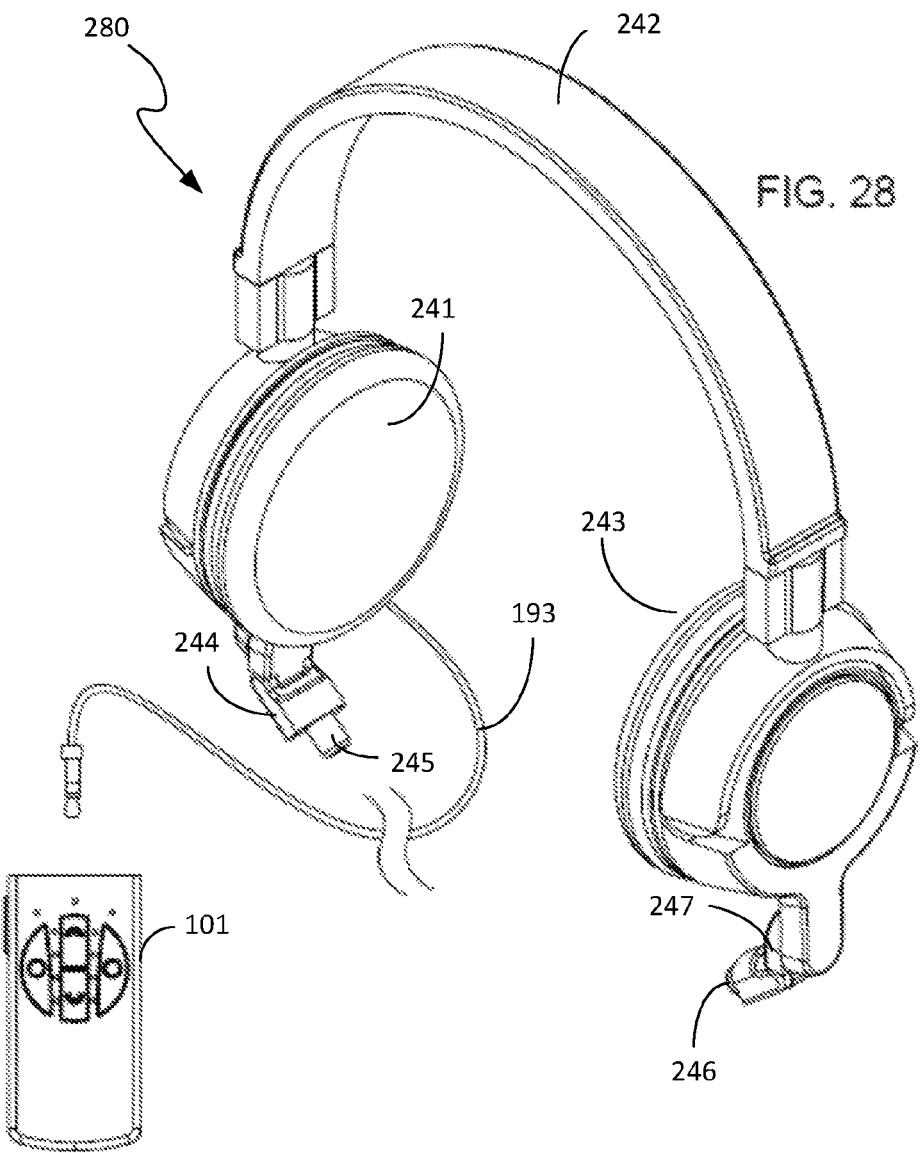
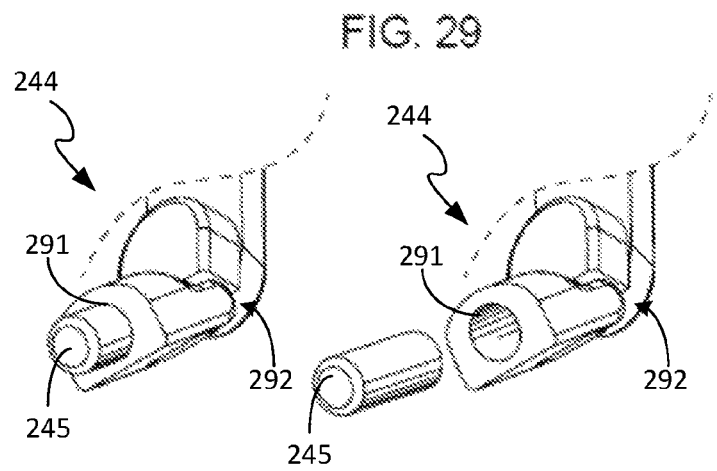

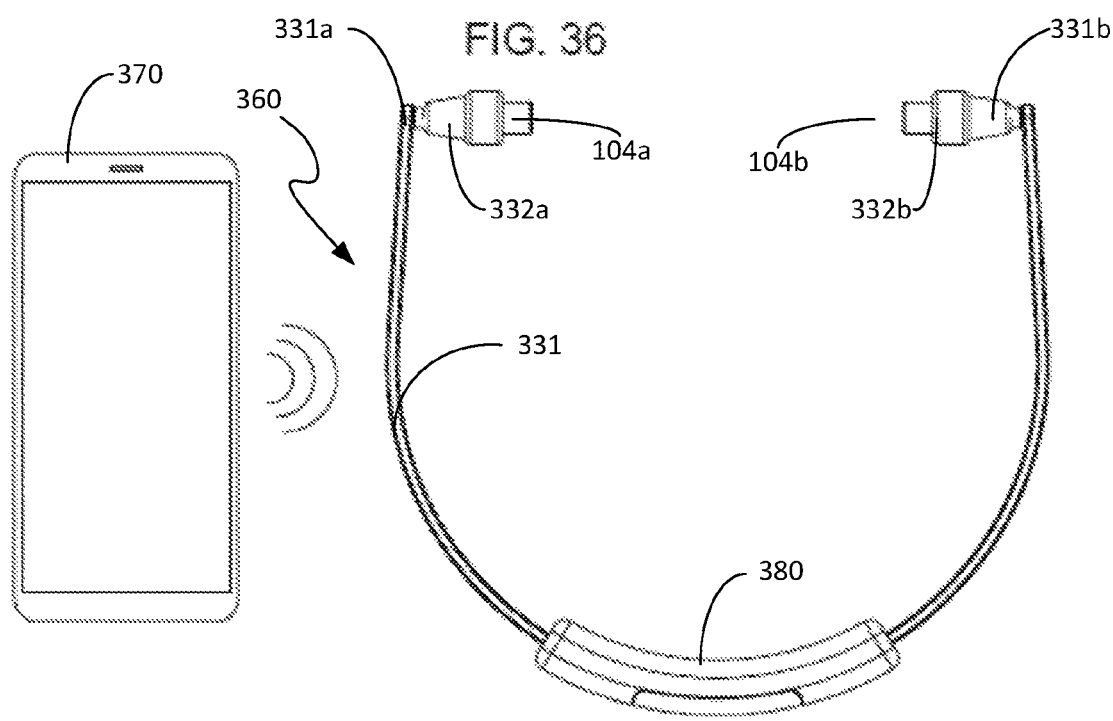
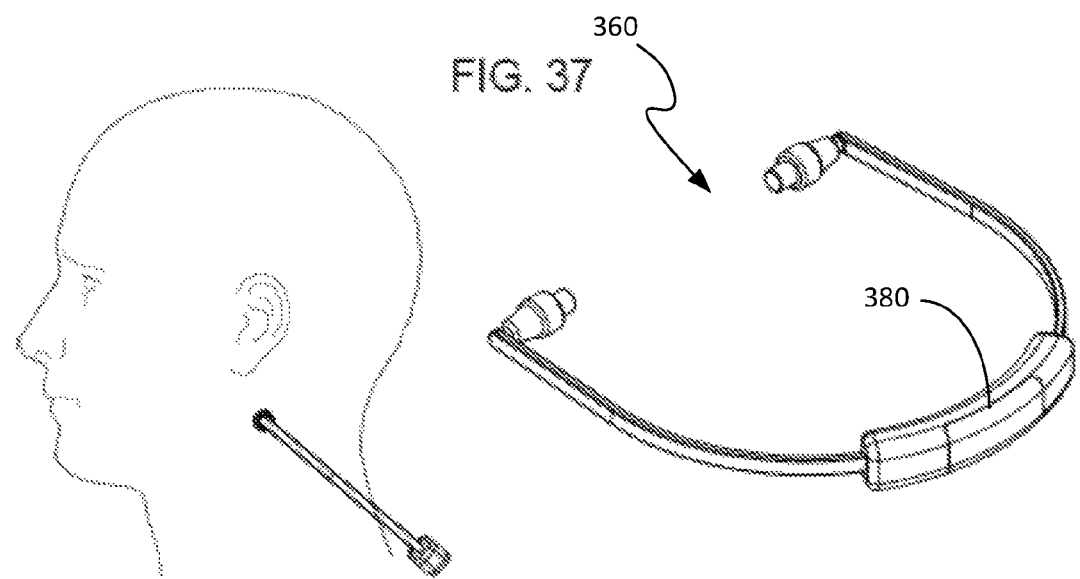

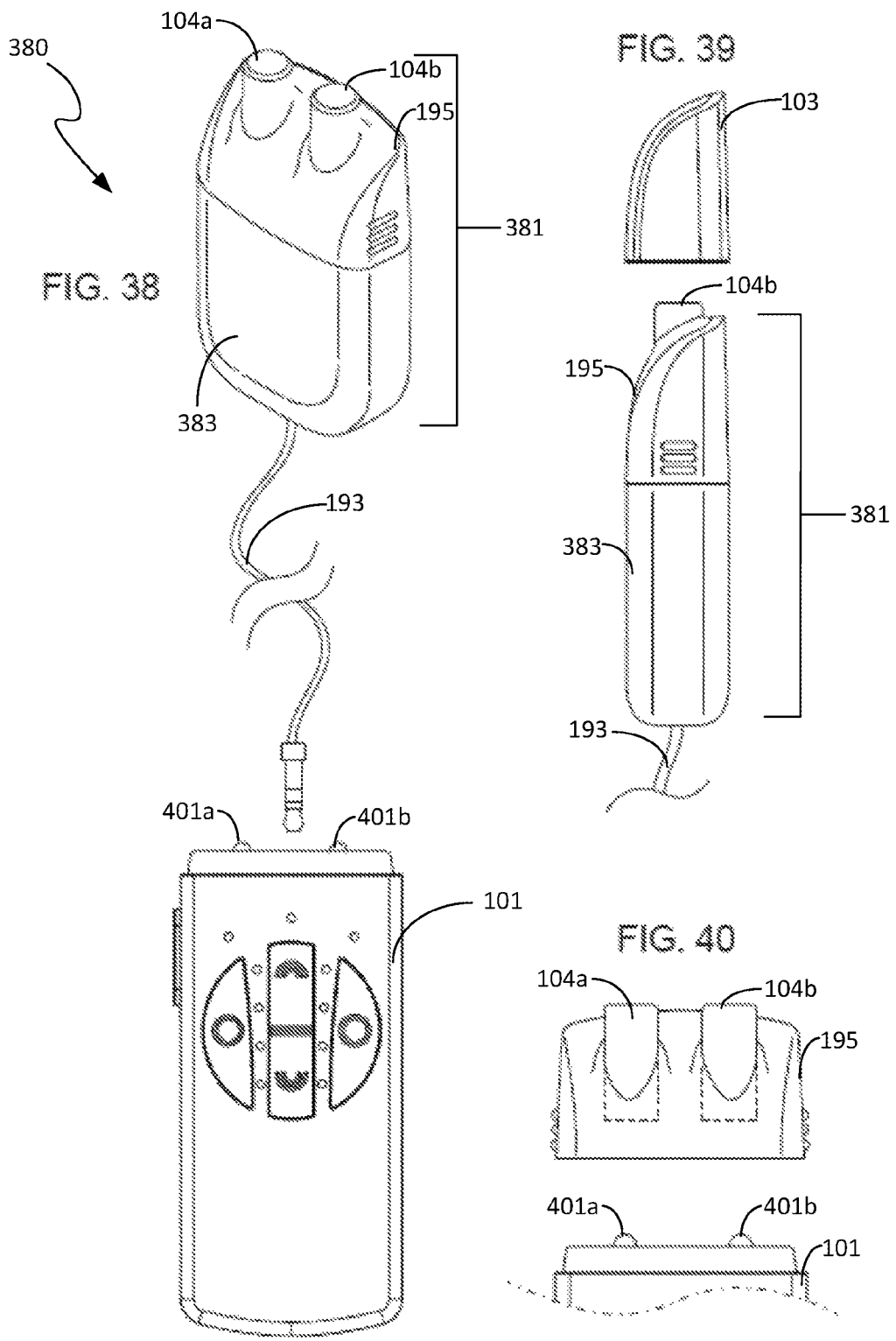

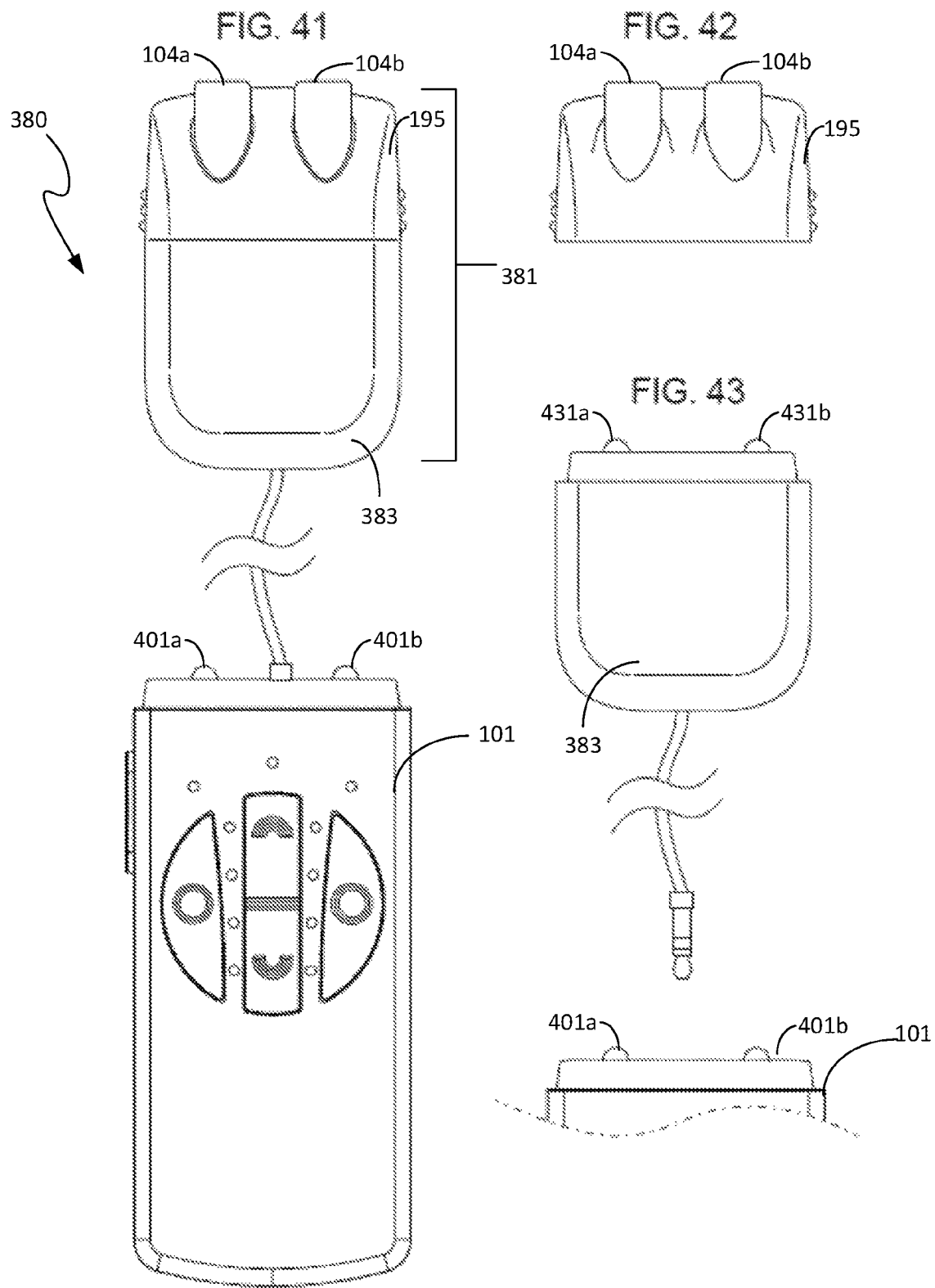

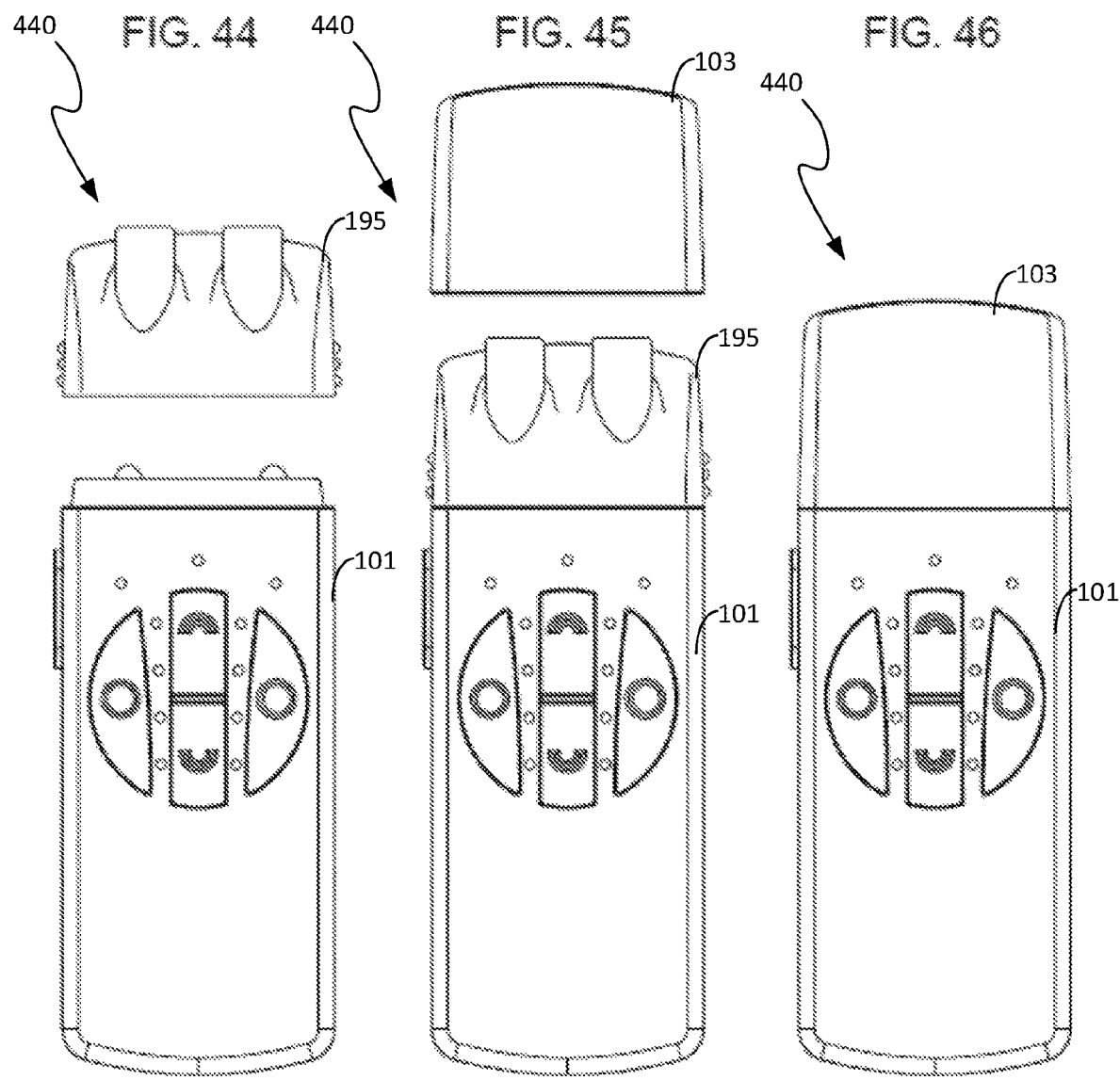

NON-INVASIVE NERVE STIMULATION DEVICES, ELECTRODE ASSEMBLIES, AND METHODS OF USE THEREOF

CROSS-REFERENCE TO RELATED APPLICATIONS

This application is a continuation of U.S. patent application entitled "NON-INVASIVE NERVE STIMULATION DEVICES, ELECTRODE ASSEMBLIES, AND METHODS OF USE THEREOF" having Ser. No. 17/050,618, filed Oct. 26, 2020.

U.S. patent application Ser. No. 17/050,618 is the 35 U.S.C. § 371 national stage application of PCT Application entitled "NON-INVASIVE NERVE STIMULATION DEVICES, ELECTRODE ASSEMBLIE, AND METHODS OF USE THEREOF" having serial no. PCT/US2019/029387, filed Apr. 26, 2019.

The PCT claims priority to, and the benefit of, U.S. Provisional application entitled "ELECTRODE ASSEMBLY FOR HOLD-IN-PLACE NON-INVASIVE ELECTRICAL NERVE STIMULATION" having Ser. No. 62/663,154, filed Apr. 26, 2018 and U.S. Provisional application entitled 'ELECTRODE ASSEMBLY FOR NON-INVASIVE VAGUS NERVE STIMULATION THROUGH THE NECK' having Ser. No. 62/663,186, filed Apr. 26, 2018.

U.S. patent application Ser. No. 17/050,618, PCT Application No. PCT/US2019/029387, and U.S. Provisional Application Nos. 62/663,154 and 62/663,186 are herein incorporated by reference in their entireties.

TECHNICAL HELD

The present disclosure relates to nerve stimulation devices and methods for performing non-invasive nerve stimulation, and in particular to devices and methods that are well suited for non-invasive stimulation of the target nerve junction containing the great auricular nerve (GAN) and the auricular branch of the vagus nerve (ABVN).

BACKGROUND OF THE DISCLOSURE

The vagus nerve controls the body's natural relaxation response, or the parasympathetic response (opposite of fight or flight response). Vagus nerve stimulators are typically implanted devices used to treat epilepsy and drug-resistant depression. However, researchers have discovered that the vagus nerve can be stimulated non-invasively by placing electrodes in and around the ear, and/or on the neck. When the vagus nerve is stimulated, the body's natural relaxation response is activated, and heart rate, blood pressure, respiratory rate, and even muscle tension can drop.

Vagus nerve stimulators have great potential to eliminate the effects of anxiety in subjects, but current electrode designs are extremely uncomfortable. One known metal electrode used to stimulate the vagus nerve through the ear is incorporated into an earbud that is inserted into the ear of the subject. The earbud, however, often delivers a painful shock to the ear. Another known earbud that is used to stimulate the vagus nerve in the left ear has to be soaked in a saline solution to work properly. A known handheld vagus nerve stimulator that is designed to be placed on the neck uses "sticky electrodes" that are covered in a sticky gel (similar to standard TENS electrode pads) so that they will remain in place once properly positioned on the neck. Use of the sticky gel electrodes typically requires skin preparation, such as shaving and cleansing with alcohol. Sticky electrodes are generally too irritating for long-term use. Additionally, sticky electrodes have to be large to provide sufficient surface area to cause them to stick to the skin and remain in place. Their large size makes it difficult or impossible to avoid placing them in contact with areas outside of the target region, which often results in muscle contraction in the neck of the subject. Another known handheld vagus nerve stimulator is designed to be held in place against the neck over the target region, and uses electrodes that must be soaked in a wet gel solution (similar to ultrasound gel) before use.

A need exists for a non-invasive nerve stimulator device that is suitable for performing non-invasive nerve stimulation of one or both of the great auricular nerve (GAN) and the auricular branch of the vagus nerve (ABVN). In some aspects, a need exists for non-invasive nerve stimulator device that is easy and comfortable to use. In some aspects, a need exists for non-invasive nerve stimulator device that avoids delivering painful shocks to the subject. In some aspects, a need exists for non-invasive nerve stimulator device that does not require soaking of the electrodes in saline solutions or covering the electrodes in sticky or wet gels. In some aspects, a need exists for non-invasive nerve stimulator device that does not require preparation of the subject's skin before use. In some aspects, a need exists for non-invasive nerve stimulator device that reduces the chance of causing muscle contraction in the neck of the subject during use.

SUMMARY OF THE DISCLOSURE

In various aspects, nerve stimulation devices, electrode assemblies for nerve stimulation devices, and methods of non-invasive nerve stimulation are provided that overcome one or more of the aforementioned deficiencies.

In some aspects, a nerve stimulation device is provided for non-invasive nerve stimulation of one or both of the great auricular nerve (GAN) and the auricular branch of the vagus nerve (ABVN) by targeting a target nerve junction containing the GAN and the ABVN in a neck of a subject in need thereof. The nerve stimulation device can include (i) a controller; (ii) an electrical waveform generator in communication with and controlled by the controller, the electrical waveform generator being configured to output an alternating current (AC) waveform from an output terminal of the electrical waveform generator; (iii) an electrode support structure; and (iv) at least first and second dry electrolyte electrodes coupled to the electrode support structure and electrically coupled to the output terminal of the electrical waveform generator. In some aspects, the dry electrolyte electrodes include (a) an electrically-conductive material, (b) a first end that is adapted to be placed in contact with a skin in the neck of the subject at the target nerve junction containing the great auricular nerve and the auricular branch of the vagus nerve, and (c) a second end opposite the first end, the second end adapted to be electrically coupled to the output terminal. In some aspects, the length of each dry electrolyte electrode defined as a distance between the first end and the second end of each dry electrolyte electrode is such that, when the device is in use, the device stimulates one or both of the GAN and the ABVN at the target nerve junction containing the great auricular nerve and the auricular branch of the vagus nerve in the neck of the subject while minimizing the occurrence of hot spots between the skin and the first end of the dry electrolyte electrode.

In some aspects, electrode assemblies are provided for use in the devices described herein. Methods of using the devices and assemblies are also provided, e.g. for non-invasive nerve stimulation of an upper branch of a vagus nerve in a neck of a subject in need thereof.

Other systems, methods, features, and advantages of the nerve stimulation devices, electrode assemblies, and methods of use thereof will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 1-5 are front perspective (FIG. 1), right side perspective (FIG. 2), back perspective (FIG. 3), top perspective (FIG. 4), and end perspective (FIG. 5) views of a first exemplary nerve stimulation device including a controller module, an electrode support structure and a removable protective cap according to various aspects of the disclosure.

FIG. 8 is a front perspective view of a top portion of the electrode support structure shown in FIGS. 6 and 7 with the first and second dry electrolyte electrodes positioned above, and in alignment with, the respective receptacles of the electrode support structure.

FIG. 9 is a top plan view of the top portion of the electrode support structure shown in FIG. 8 with the first and second dry electrolyte electrodes positioned above, and in alignment with, the respective receptacles of the electrode support structure.

FIG. 10 is a side cross-sectional view of the top portion of the electrode support structure and the first and second dry electrolyte electrodes positioned above the respective receptacles taken along line A-A' in FIG. 9.

FIGS. 11 and 12 are, respectively, left and right top perspective views, respectively, of a portion controller module of the nerve stimulation device shown in FIG. 1-5 separated from, and in alignment with, the removable electrode holder of the nerve stimulation device.

FIG. 21 is a fully exploded front perspective view of the nerve stimulation device shown in FIG. 19.

FIG. 22 is a front perspective view of an electrical coupling unit of the nerve stimulation device shown in FIGS. 19-21.

FIG. 23 is a fully exploded front perspective view of the nerve stimulation device shown in FIG. 21 with the electrical coupling unit of the electrode support structure shown in FIGS. 21 and 22 removed from the electrode support structure and a direct coupling between a removable electrode holder of the electrical support structure and the controller module that obviates the need for the electrical cable shown in FIG. 21.

FIGS. 24 and 25 are, respectively, front and right side perspective views of a headset including the nerve stimulation device in accordance with another representative embodiment. In accordance with this representative embodiment, the controller and the electrical waveform generator of the nerve stimulation device are incorporated into the headset.

FIG. 28 is a front perspective view of a headset including the electrode support structure of the nerve stimulation device in accordance with another representative embodiment. In accordance with this representative embodiment, the controller and the electrical waveform generator are contained in the controller module housing, which is external to the headset and electrically coupled to the headset via an electrical cable.

FIG. 29 is front perspective views of the first electrode holder shown in FIGS. 24 and 28 in accordance with a representative embodiment with the dry electrolyte electrode held in the receptacle of the holder and with the dry electrolyte electrode outside of and aligned with the receptacle immediately before or after insertion.

FIG. 36 is a front perspective view of a neck attachment including the nerve stimulation device in accordance with another representative embodiment that is similar to the neck attachment shown in FIGS. 33 and 34 except that the controller module of the nerve stimulation device is incorporated into the neck attachment shown in FIG. 36 and is wireless controlled via a smart phone or a separate wireless-enabled controller.

FIG. 37 is a left side perspective view of the neck attachment shown in FIG. 36 properly placed on a subject.

FIG. 38 is a front perspective view of the nerve stimulation device in accordance with another representative embodiment including a controller module, an electrode support structure and an electrical cable that can be used to electrically connect the electrode support structure to the controller module.

FIG. 39 is a left side perspective view of the nerve stimulation device shown in FIG. 38 with a removable protective cap position above, and in alignment with, the electrode support structure; the controller module is not shown in FIG. 39 for ease of illustration.

FIG. 40 is a front perspective view of the nerve stimulation device shown in FIG. 38 with the electrical coupling unit of the electrode support structure shown in FIG. 38 removed to allow the removable electrode holder of the electrode support structure to couple directly with the controller module, thereby obviating the need for the electrical cable.

FIG. 41 is a front perspective view of the nerve stimulation device shown in FIG. 38 with the controller module and the electrode support structure electrically interconnected via the electrical cable.

FIG. 42 is a front perspective view of the removable electrode holder of the electrode support structure shown in FIG. 38.

FIG. 43 is a front perspective view of the electrical coupling unit of the electrode support structure shown in FIG. 38 and an upper portion of the controller module being electrically connected via an electrical cable.

FIG. 44 is a front perspective exploded view of the nerve stimulation device in accordance with another representative embodiment in which the removable electrode holder couples directly with the controller module without the need for an electrical cable.

FIG. 45 is a front perspective view of the nerve stimulation device shown in FIG. 44 with the removable electrode holder coupled directly with the controller module and with a removable protective cap positioned above, and aligned with, the removable electrode holder.

FIG. 46 is a front perspective view of the nerve stimulation device shown in FIG. 45 with the removable protective cap removably secured to the removable electrode holder.

DETAILED DESCRIPTION

Figure 1:
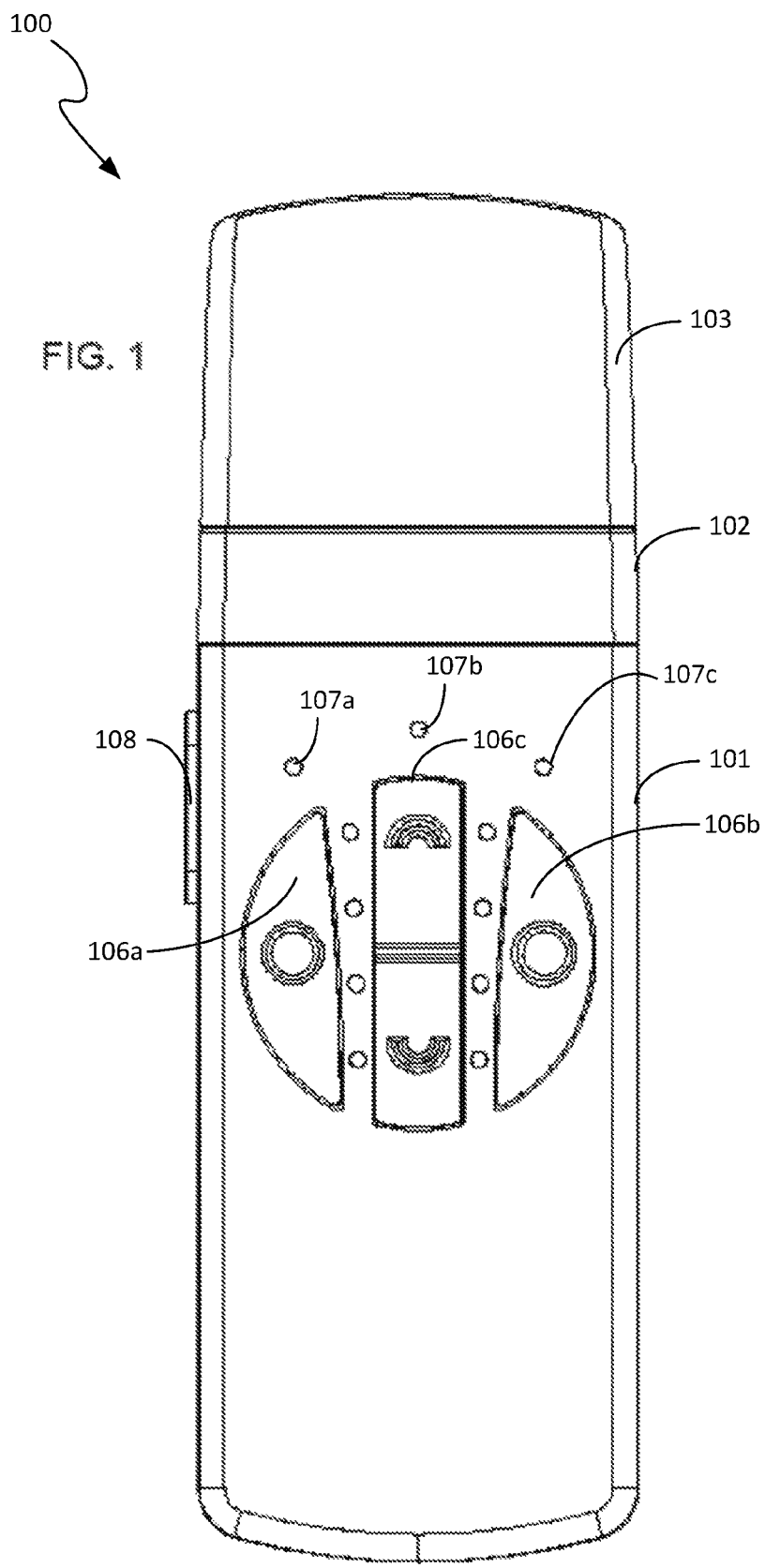
Figure 2:
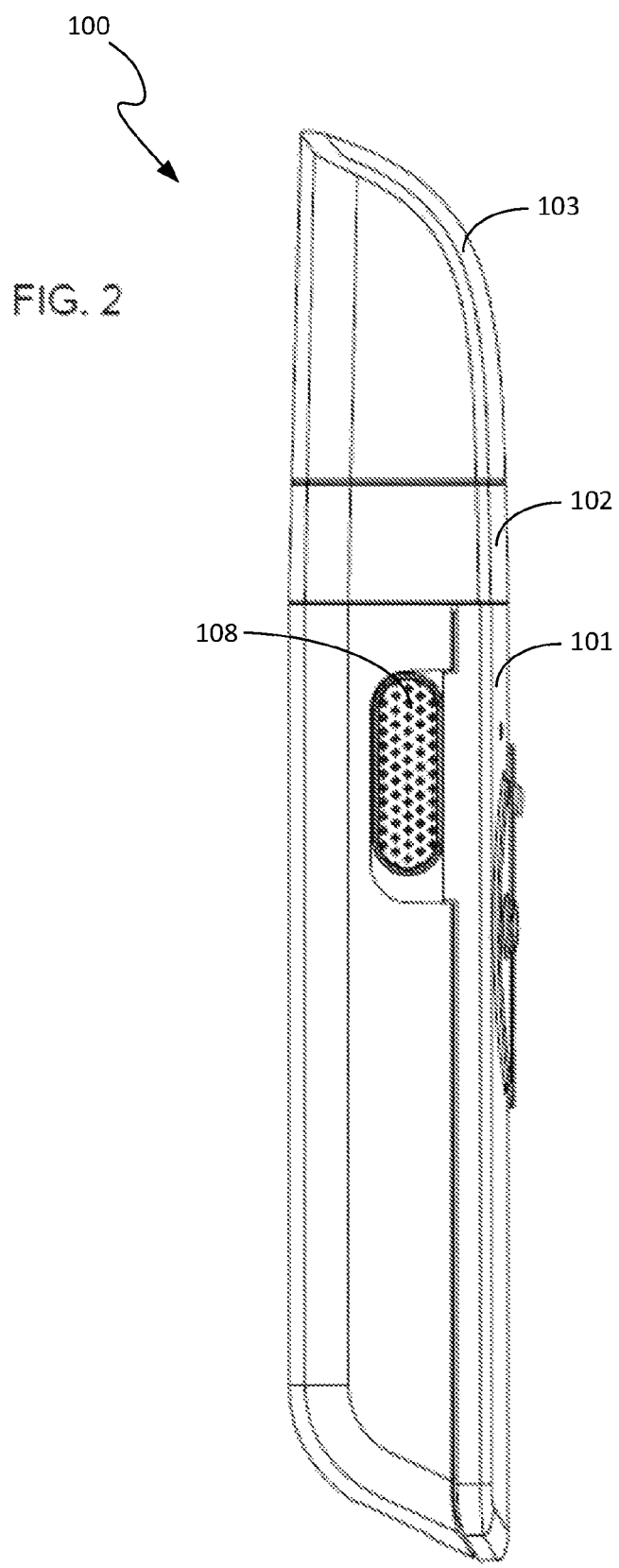

The present disclosure is directed to nerve stimulation devices and methods for performing non-invasive nerve stimulation that are particularly well suited for performing non-invasive stimulation of one or both of the great auricular nerve and the auricular branch of the vagus nerve through the target nerve junction containing the great auricular nerve and the auricular branch of the vagus nerve in the neck of the subject. In some aspects, the nerve stimulation device uses dry electrolyte electrodes that are comfortable to use and suitable for long-term use. In some aspects, the nerve stimulation device uses dry electrolyte electrodes that avoid delivering painful shocks to the subject. The dry electrolyte electrodes can be used, at least in some aspects, without requiring soaking of the electrodes in saline solutions or covering them in sticky or wet gels. In some aspects, method of using the dry electrolyte electrodes do not require skin preparation. In some aspects, the electrodes described herein can avoid causing muscle contraction in areas outside of the targeted areas of the target nerve junction containing the great auricular nerve and the auricular branch of the vagus nerve during use.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting. The skilled artisan will recognize many variants and adaptations of the embodiments described herein. These variants and adaptations are intended to be included in the teachings of this disclosure.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant specification should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Embodiments of the present disclosure will employ, unless otherwise indicated, techniques of electrical and device engineering, and methods of non-invasive medical treatments, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to about 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some embodiments, the term "about" can include traditional rounding according to significant figures of the numerical value. In addition, the phrase "about 'x' to 'y'", where 'x' and 'y' are numerical values, includes "about 'x' to about 'y'".

In some instances, units can be used herein that are non-metric or non-SI units. Such units can be, for instance, in U.S. Customary Measures, e.g., as set forth by the National Institute of Standards and Technology, Department of Commerce, United States of America in publications such as NIST HB 44, NIST HB 133, NIST SP 811, NIST SP 1038, NBS Miscellaneous Publication 214, and the like. The units in U.S. Customary Measures are understood to include equivalent dimensions in metric and other units (e.g., a dimension disclosed as "1 inch" is intended to mean an equivalent dimension of "2.5 cm"; a unit disclosed as "1 pcf" is intended to mean an equivalent dimension of 0.157 kN/m3; or a unit disclosed 100° F. is intended to mean an equivalent dimension of 37.8° C.; and the like) as understood by a person of ordinary skill in the art.

Relative terms can be used to describe the various elements' relationships to one another, as illustrated in the accompanying drawings. These relative terms are intended to encompass different orientations of the device and/or elements in addition to the orientation depicted in the drawings.

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

It will be understood that when an element is referred to as being "connected to" or "coupled to" or "electrically coupled to" another element, it can be directly connected or coupled, or intervening elements can be present.

The term "memory" or "memory device," as those terms are used herein, are intended to denote a computer-readable storage medium that is capable of storing computer instructions, or computer code, for execution by one or more processors. References herein to "memory" or "memory device" should be interpreted as one or more memories or memory devices. The memory can, for example, be multiple memories within the same computer system. The memory can also be multiple memories distributed amongst multiple computer systems or computing devices.

A "controller," as that term is used herein encompasses an electronic component that is able to execute a computer program or executable computer instructions. References herein to "a controller" should be interpreted as one or more controllers or processors. The controller can be, for instance, a microcontroller, a microprocessor or a multi-core processor.

Exemplary, or representative, aspects will now be described with reference to the figures, in which like reference numerals represent like components, elements or features. It should be noted that features, elements or components in the figures are not intended to be drawn to scale, emphasis being placed instead on demonstrating inventive principles and concepts.

FIGS. 1-5 show, respectively, front perspective, right side perspective, back perspective, top perspective and end perspective views of the nerve stimulation device 100 in accordance with a representative embodiment including a controller module housing 101 that houses a controller (not shown) and an electrical waveform generator (not shown), an electrode support structure 102 and a removable protective cap 103. The controller and the electrical waveform generator are described below in more detail with reference to FIG. 47, which is block diagram of the electrical circuitry that can be housed inside of the controller module housing 101 shown in FIGS. 1-5.

Figure 6:
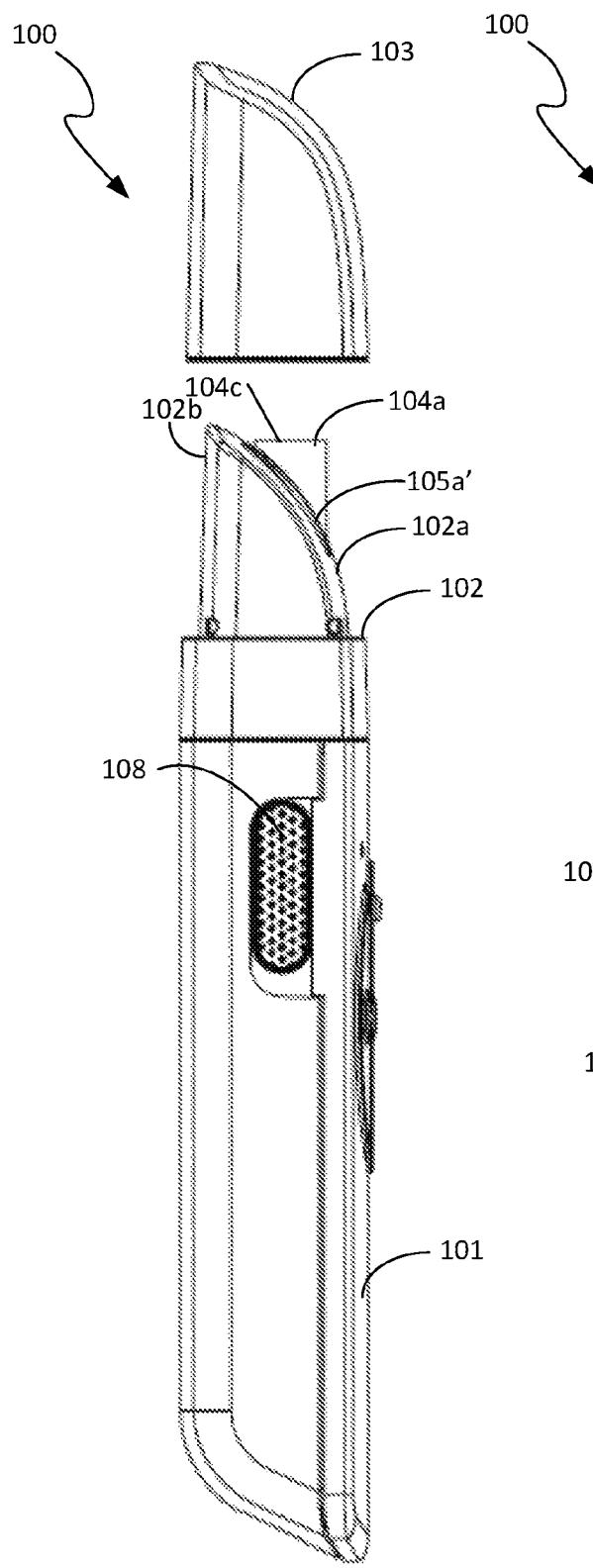
FIG. 6 is a right side perspective view of the first exemplary nerve stimulation device in FIGS. 1-5 with the protective cap removed from the electrode support structure of the nerve stimulation device to show first and second dry electrolyte electrodes held in respective receptacles of the electrode support structure.
Figure 7:
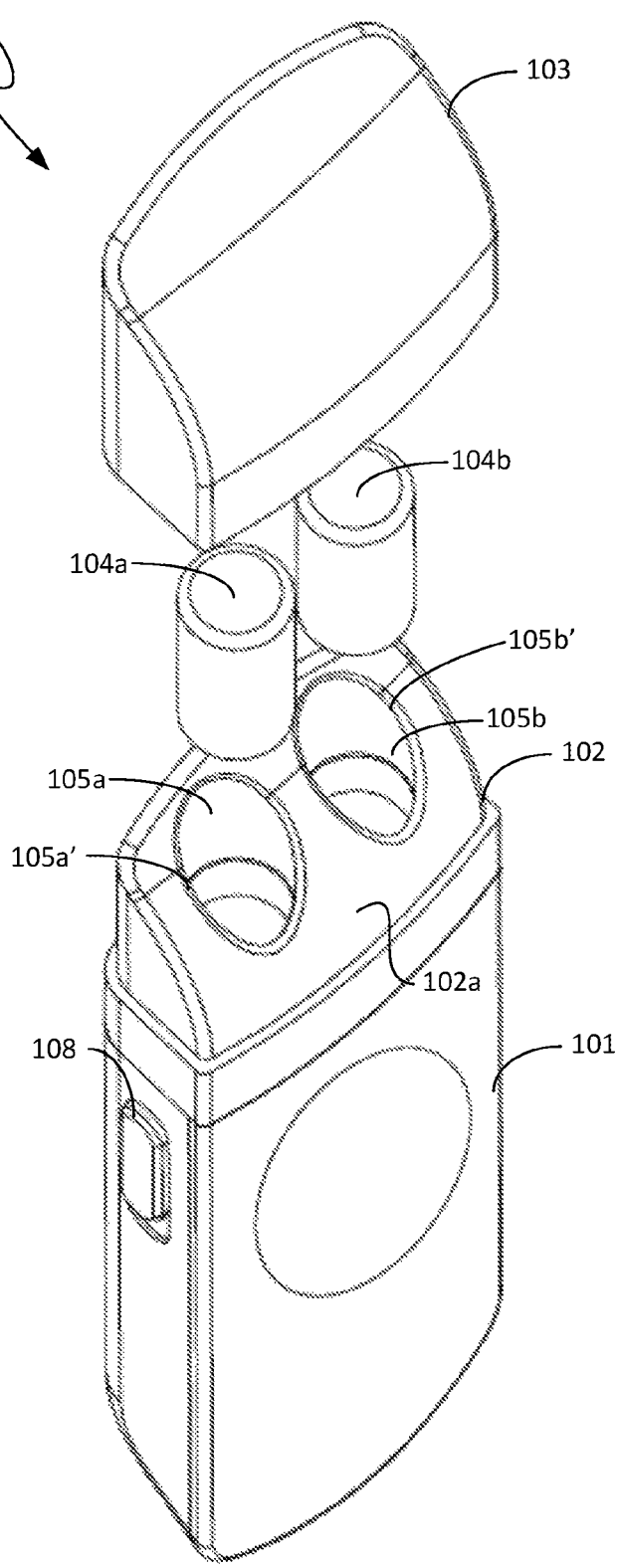
FIG. 7 is a front perspective view of the first exemplary nerve stimulation device in FIG. 6 with the first and second dry electrolyte electrodes positioned above the respective receptacles of the electrode support structure in alignment with the respective receptacles.

FIG. 6 shows a right side perspective view of the nerve stimulation device 100 shown in FIGS. 1-5 with the removable protective cap 103 removed from the electrode support structure 102 of the nerve stimulation device 100 to show first and second dry electrolyte electrodes 104a and 104b, respectively. FIG. 7 shows a front perspective view of the nerve stimulation device 100 shown in FIG. 6 with the first and second dry electrolyte electrodes 104a and 104b, respectively, positioned above respective receptacles 105a and 105b of the electrode support structure 102 in alignment with the respective receptacles 105a and 105b. The first and second electrodes 104a and 104b, can be held in receptacles 105a and 105b, respectively, of the electrode support structure 102.

It can be seen from FIGS. 6 and 7 that the rims 105a' and 105b' of the first and second receptacles 105a and 105b, respectively, are formed in a curved surface 102a of the electrode support structure 102 that meets a flat back surface 102b of the electrode support structure 102. The first end 104c of the first dry electrolyte electrode 104a extends away from the rim 105a' such that it is disposed to be pressed against the skin of the subject. The flat back 102b of the electrode support structure 102 provides mechanical support for the dry electrolyte electrodes 104a and 104b so that pressing of the first ends 104c and 104d of the dry electrolyte electrodes 104a and 104b, respectively, do not break, bend or otherwise damage the dry electrolyte electrodes 104a and 104b.

With reference again to FIG. 1, the controller module housing 101 can have buttons 106a and 106b that can be used by a user to select the type of waveform that is generated by the electrical waveform generator. In accordance with a representative embodiment, either of the buttons 106a and 106b can be used to make the waveform selection, causing one of three light emitting diodes (LEDs) 107a, 107b and 107c to light up to indicate which of three waveforms have been selected. In accordance with this embodiment, the waveforms are biphasic waveforms, but the inventive principles and concepts are not limited with respect to the types of waveforms or the number of waveform selections that can be generated by the electrical waveform generator.

The controller module housing 101 can have a button 106c that can be pressed on an upper portion thereof or on a lower portion thereof to increase or decrease, respectively, the amplitude of the waveform that is output from the output terminal of the electrical waveform generator. Increasing or decreasing the amplitude of the waveform increases or decreases, respectively, the voltage of the waveform, which, in turn, increases or decreases, respectively, the electrical current on the dry electrolyte electrodes 104a and 104b, i.e., the electrical current being applied by the dry electrolyte electrodes 104a and 104b to the skin of the subject. A switch 108 can be slid to an upper position or to a lower position to cause power to be supplied to or removed from the electrical circuitry (not shown) inside of the controller module housing 101. In accordance with a representative embodiment, the controller module housing 101 includes a Universal Serial Bus (USB) port 109 that is used to charge a power source (not shown) housed inside of the controller module housing 101.

The receptacles 105a and 105b (FIG. 7) that hold the dry electrolyte electrodes 104a and 104b, respectively, are typically coated with an electrically-conductive material, such as metal, for example. The receptacles 105a and 105b are typically complementary in shape and size to the shape and size of the dry electrolyte electrodes 104a and 104b, respectively, such that the dry electrolyte electrodes 104a and 104b are form fitted, or friction fitted, to the receptacles 105a and 105b, respectively. In other words, insertion of the dry electrolyte electrodes 104a and 104b into the receptacles 105a and 105b, respectively, can create a snug fit that holds the dry electrolyte electrodes 104a and 104b in the receptacles 105a and 105b, respectively. The lower and inside surfaces of the receptacles 105a and 105b can have approximately the same widths or diameters as the dry electrolyte electrodes 104a and 104b, respectively, to ensure that electrical current spreads very quickly from the lower and inside surfaces of the receptacles 105a and 105b throughout the dry electrolyte electrodes 104a and 104b, respectively. It should be noted that while FIG. 7 shows the dry electrolyte electrodes 104a and 104b being cylindrical in shape, the dry electrolyte electrodes 104a and 104b can have other shapes or cross-sections, such as rectangular and square, for example.

FIG. 8 shows a front perspective view of a top portion of the electrode support structure 102 shown in FIGS. 6 and 7 with the first and second dry electrolyte electrodes 104a and 104b, respectively, positioned above, and in alignment with, the respective receptacles 105a and 105b of the electrode support structure 102. FIG. 9 shows a top plan view of the top portion of the electrode support structure shown in FIG. 8 with the first and second dry electrolyte electrodes 104a and 104b, respectively, positioned above, and in alignment with, the respective receptacles 105a and 105b, respectively, of the electrode support structure 102. FIG. 10 shows a side cross-sectional view of the top portion of the electrode support structure and the first and second dry electrolyte electrodes positioned above the respective receptacles taken along line A-A' in FIG. 9.

With reference to FIG. 8, in accordance with this representative embodiment, when the first and second dry electrolyte electrodes 104a and 104b are held in the first and second receptacles 105a and 105b, respectively, central axes 111a and 111b of the first and second dry electrolyte electrodes 104a and 104b, respectively, are separated from one another by a distance, D, that ranges from 0.1 centimeters (cm) to 50 cm, about 1 cm to about 10 cm, or about 1 cm to about 5 cm. Keeping this distance within this range can help ensure that when a subject is using the nerve stimulation device 100 to stimulate the one or both of the GAN and the ABVN, the dry electrolyte electrodes 104a and 104b do not come into contact with areas outside of the target area and stimulate other nerves or muscles, resulting in muscle contraction. As will be described below in more detail, users of the nerve stimulation device 100 will be provided with a user's manual that will instruct the user on how to perform treatment, including the location on the neck at which to place the dry electrolyte electrodes 104a and 104b to perform treatment. Due to the relatively small distance, D, and the relative ease of the user locating the target area with guidance from the user's manual, the likelihood of the dry electrolyte electrodes 104a and 104b being placed on areas of the skin that are outside of the target area is relatively small.

With reference to FIG. 10, the distance, D, between a first end 104c of the first dry electrolyte electrode 104a and a second end 104d of the first dry electrolyte electrode 104a is sufficiently great that electrical current passing from the electrically-conductive inside surface of the receptacle 105a has time to spread out throughout the material including the dry electrolyte electrode 104a before coming into contact with the subject's skin. This reduces or eliminates the possibility of electrical shocks to the subject's skin, also commonly referred to as hotspots. With metal electrodes, current has very little time to spread out before passing from the electrode into the subject's skin, which often results in uncomfortable, and even painful, hotspots occurring. With hydrogel electrodes of the type that are typically used to stimulate nerves, the hydrogel is typically a relatively thin coating on top of a metal electrode. While the thin coatings help reduce the occurrence of hotspots, hotspots still occur too often.

In contrast to these thin hydrogel coatings, the dry electrolyte electrode 104a has a length, L, defined as the distance between the first end 104a and the second end 104d. This length, L, can be sufficiently long to minimize or prevent the occurrence of hotspots by allowing the current to evenly distribute throughout the electrode. In some instances, the length, L, can range from about 0.5 cm to about 10 cm, about 1 cm to about 10 cm, or about 1 cm to about 5 cm. These dimensional ranges apply to the second dry electrolyte electrode 104b as well, although it is not visible in the side cross-sectional view shown in FIG. 10. The dry electrolyte electrodes 104a and 104b are made of an electrolyte material, which is typically a hydrogel material, such as agarose, for example. The material composition of the dry electrolyte electrodes 104a and 104b is described below in more detail under the heading "MATERIAL COMPOSITION OF THE ELECTRODES."

FIGS. 11 and 12 show left and right top perspective views, respectively, of a portion of the controller module housing 101 of the nerve stimulation device 100 shown in FIG. 1-5 separated from, and in alignment with, the electrode support structure 102 of the nerve stimulation device 100. The electrode support structure 102 is removable, as shown in FIG. 12, and has an upper portion and a lower portion. The upper portion has the receptacles 105a and 105b formed in it and that serves as the electrode holder for holding the dry electrolyte electrodes 104a and 104b, respectively. The lower portion is an electrical coupling unit that electrically couples the output terminal of the electrical waveform generator housed in the controller module housing 101 with the receptacles 105a and 105b of the electrode holder. In accordance with this representative embodiment, the electrical coupling unit comprises an auxiliary connector 112 that mates with an auxiliary receptacle (not shown) comprised in the controller module housing 101. In accordance with this representative embodiment, the controller module housing 101 has two posts 113a and 113b that mate with two complementarily-shaped openings 114a and 114b disposed in the electrical coupling unit when the controller module housing 101 and the electrode support structure 102 are mated. The mating of the posts 113a and 113b with the openings 114a and 114b, respectively, enhances the mechanical stability of the nerve stimulation device 101.

Material Composition of the Electrodes

The term "dry electrolyte electrode," as that term is used herein, denotes electrodes formed of a polymeric gel material and an electrolyte that are dry or essentially dry to the touch. The term "dry" can refer to a composition from which all or a substantial portion of any water has been removed to produce a solid phase of the composition. Although in some aspects it can be the case, the term does not require the complete absence of moisture (i.e., the electrode may have a moisture content from about 0.1% by weight to about 5% by weight or more). In some aspects, the "dry electrolyte electrode," is not a sticky electrode in that it does not stick to the skin or have any adhesion to the skin.

In some aspects, the dry electrolyte electrode is or includes an agarose electrode. In some aspects, the electrode is a linear polysaccharide that includes an electrolyte. In some aspects, the electrode can include one or more other polymers. For example, the dry electrolyte electrode can include a polymer electrode selected from the group consisting of an agarose gel, a collagen gel, a glucomannan gel, a polyacrylamide gel, a polyacrylamide-2-methylpropanesulfonic acid gel, a fibrin gel, a polyvinyl alcohol gel, a polyhydroxyethyl methacrylate gel, a silicone hydrogel, a polyvinylpyrrolidone gel, a polyethyleneglycol gel, a poly(2-acrylamide-2-methylpropanesulfonic acid) gel, an alginate gel, a carrageenan gel, a chitosan gel, a poly(N-isopropylacrylamide) gel, an acrylic acid gel, a polystyrene sulfonic acid gel, and a combination thereof.

Figure 13:
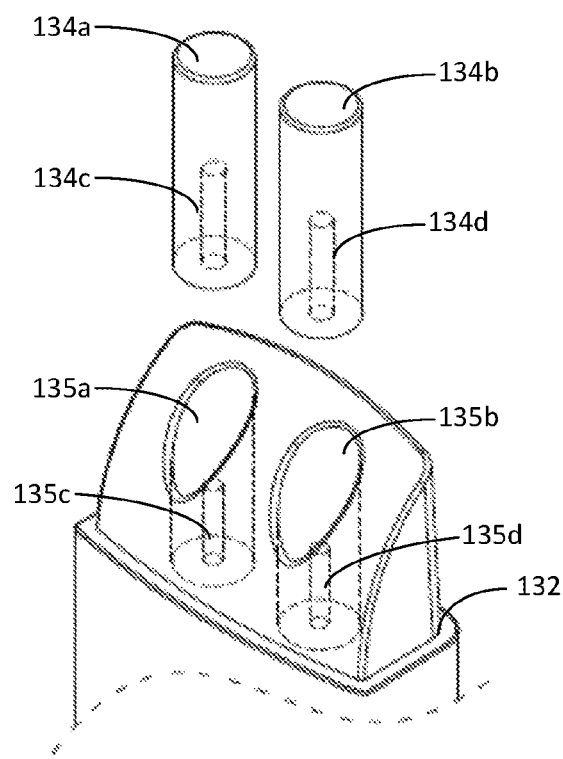
FIG. 13 is a front perspective view of a top portion of the electrode support structure of the nerve stimulation device shown in FIG. 1 in accordance with another representative embodiment with the first and second dry electrolyte electrodes positioned above, and in alignment with, the respective receptacles of the electrode support structure.
Figure 14:
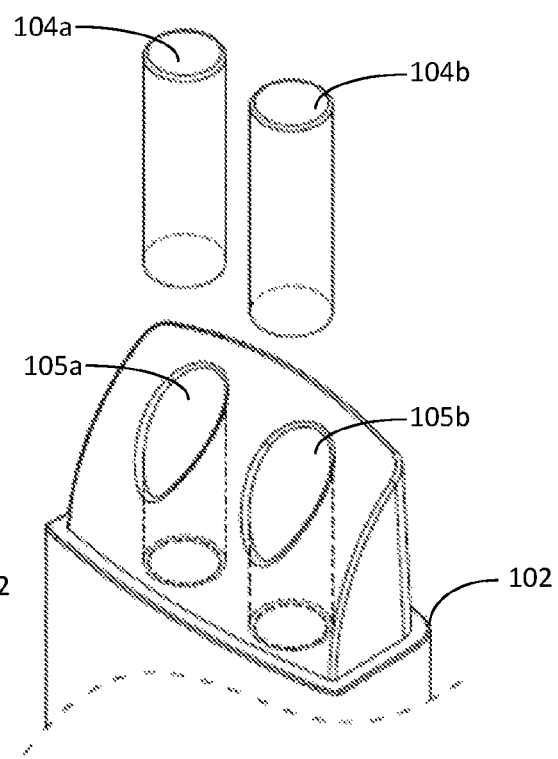
FIG. 14 is a front perspective view of a top portion of the electrode support structure of the nerve stimulation device shown in FIGS. 6 and 7 with the first and second dry electrolyte electrodes positioned above, and in alignment with, the respective receptacles of the electrode support structure.
Figure 15:
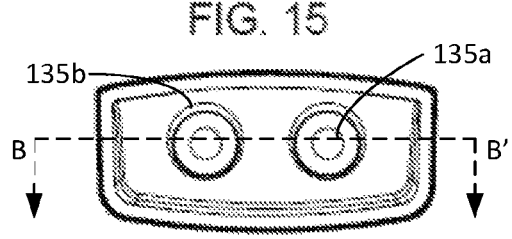
FIG. 15 is a top plan view of the top portion of the electrode support structure shown in FIG. 13 with the first and second dry electrolyte electrodes positioned above, and in alignment with, the respective receptacles of the electrode support structure.
Figure 16:
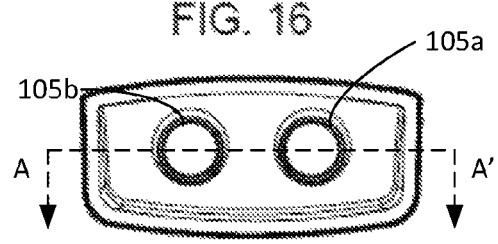
FIG. 16 is a top plan view of the top portion of the electrode support structure shown in FIG. 14 with the first and second dry electrolyte electrodes positioned above, and in alignment with, the respective receptacles of the electrode support structure.
Figure 17:
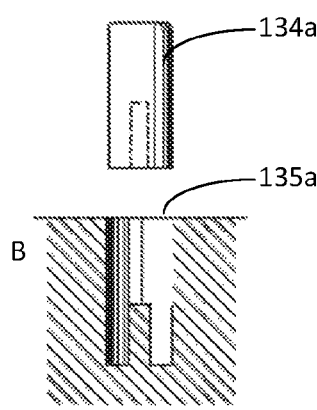
FIG. 17 is a side cross-sectional view of the top portion of the electrode support structure and the first and second dry electrolyte electrodes positioned above the respective receptacles taken along line B-B' in FIG. 15.
Figure 18:
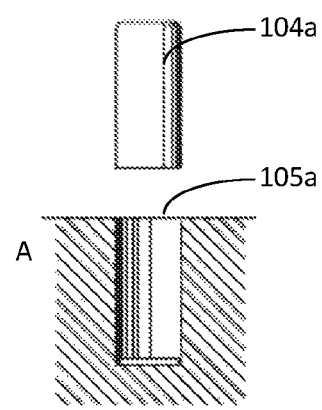
FIG. 18 is a side cross-sectional view of the top portion of the electrode support structure and the first and second dry electrolyte electrodes positioned above the respective receptacles taken along line A-A' in FIG. 16.

FIG. 13 shows a front perspective view of a top portion of the electrode support structure 132 of the nerve stimulation device 100 shown in FIG. 1 in accordance with another representative embodiment with first and second dry electrolyte electrodes 134a and 134b, respectively, positioned above, and in alignment with, respective receptacles 135a and 135b of the electrode support structure 132. FIG. 15 shows a top plan view of the electrode support structure 132 shown in FIG. 13 with the first and second dry electrolyte electrodes 134a and 134b, respectively, positioned above, and in alignment with, the respective receptacles 135a and 135b of the electrode support structure 132. FIG. 17 shows a side cross-sectional view of the top portion of the electrode support structure and the first and second dry electrolyte electrodes positioned above the respective receptacles taken along line B-B' in FIG. 15. FIGS. 14, 16 and 18 are identical to FIGS. 8, 9 and 10, respectively, and are shown beside FIGS. 13, 15 and 17, respectively, for comparison purposes.

The dry electrolyte electrodes 134a and 134b are different from the dry electrolyte electrodes 104a and 104b in that the dry electrolyte electrodes 134a and 134b have cylindrically-shaped openings 134c and 134d formed in them, respectively. The receptacles 135a and 135b have cylindrically-shaped electrically-conductive (e.g., metal) posts 135c and 135d disposed therein, respectively, that are complementary in shape and size to the cylindrically-shaped openings 134c and 134d. The lower surfaces and inside walls of the receptacles 135a and 135b also comprise the electrically-conductive material of which the posts 135c and 135d are made. The posts 135c and 135d mate with the openings 134c and 134d, respectively, when the dry electrolyte electrodes 134a and 134b are inserted into the receptacles 135a and 135b, respectively. The mating of the posts 135c and 135d with the openings 134c and 134d, respectively, ensures that electrical current spreads quickly and is evenly distributed over the material including the dry electrolyte electrodes 134a and 134b to reduce or eliminate the likelihood of hotspots occurring during treatment.

In some aspects, the dry electrolyte electrode and the spreading of the current to avoid hotspots promotes comfort for the user during use, e.g. comfort relative to state-of-the-art electrode designs such as standard TENS stimulation electrodes (i.e., 2"×2", NuCalm), metal electrodes (i.e., NuFace, CerboMed), metal electrodes coated in a thin layer of wet gel (i.e., gammaCore), conductive silicone coated in a wet saline solution (i.e., Nervana). The electrode material in each electrode design has a unique resistivity, skin-electrolyte impedance, and surface area of contact between the skin and the electrolyte. Current density at the skin-electrolyte interface is the most important factor when designing for maximum comfort. To test which electrode design is the most comfortable during stimulation, all electrodes should be tested at the same values for current density at the skin-electrolyte interface. Current density can be calculated by measuring the amount of current being delivered at the skin interface and dividing that value by the area of contact between the electrode and the skin. For example, an electrode that has a skin contact area of 1 square centimeter and delivers 2 mA to the skin will have a current density of 2 mA/cm2.

Figure 19:
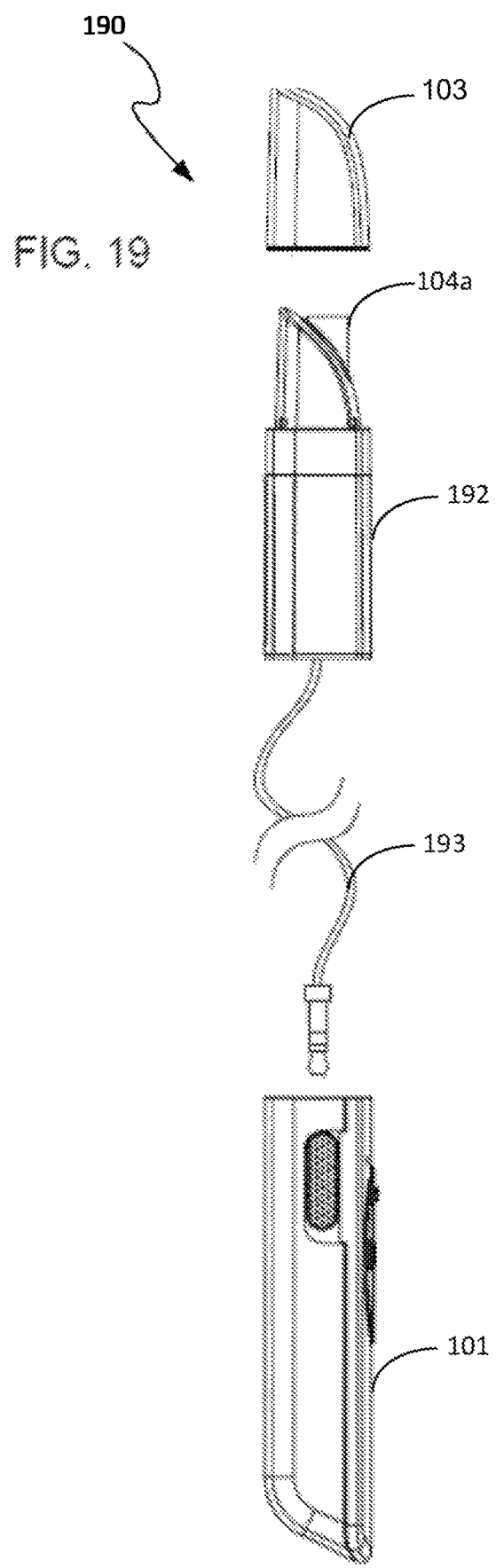
FIG. 19 is a partially exploded right side perspective view of the nerve stimulation device in accordance with another representative embodiment with the removable protective cap removed and with the electrode support structure electrically coupled to the controller module by an electrical cable.
Figure 20:
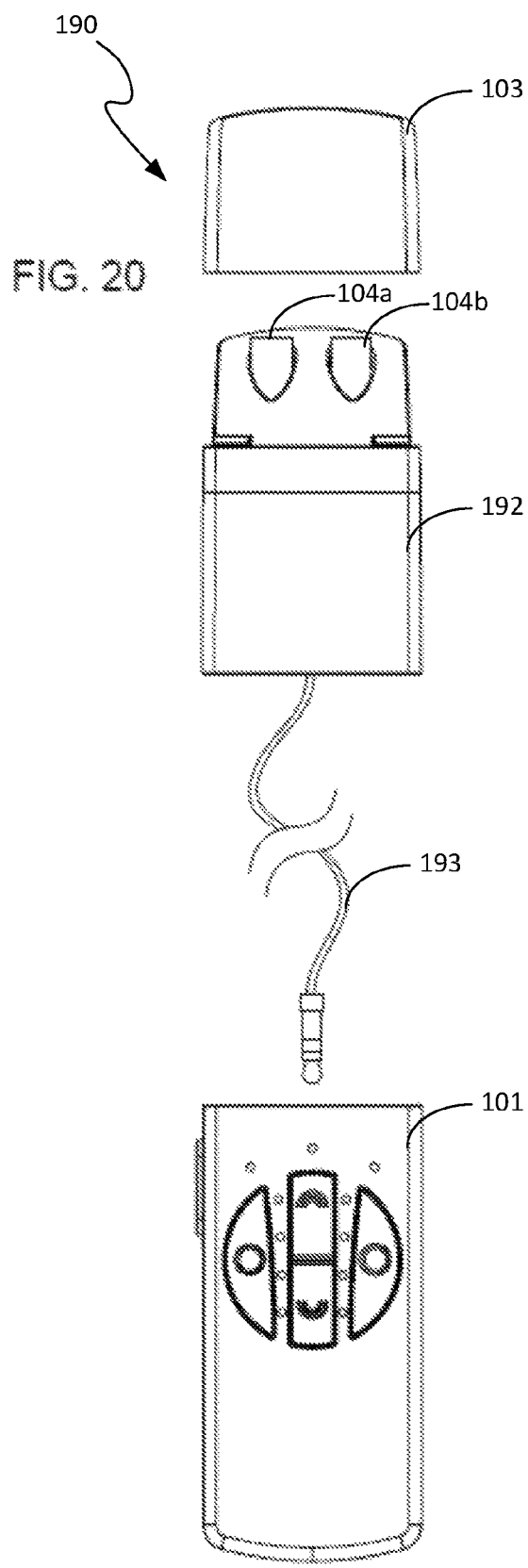
FIG. 20 is a partially exploded front perspective view of the nerve stimulation device shown in FIG. 19.

FIG. 19 shows a partially exploded right side perspective view of the nerve stimulation device 190 in accordance with another representative embodiment with the removable protective cap 103 removed and with the electrode support structure 192 electrically coupled to the controller module housing 101 by an electrical cable 193. FIG. 20 shows a partially exploded front perspective view of the nerve stimulation device 190 shown in FIG. 19. FIG. 21 shows a fully exploded front perspective view of the nerve stimulation device shown in FIG. 19. FIG. 22 shows a front perspective view of an electrical coupling unit 195 of the nerve stimulation device 190 shown in FIGS. 19-21.

In accordance with this representative embodiment, the electrode support structure 192 is longer in the lengthwise direction than the electrode support structure 102 shown in FIG. 6 to allow a user to grip the lower portion of the electrode support structure 192 in his or her fingers and position it to place the exposed ends of the dry electrolyte electrodes 104a and 104b on the skin of the neck in the target area. The controller module housing 101 shown in FIG. 19 can be identical to, and house the same components as, the controller module housing 101 shown in FIG. 1. Connecting the electrode support structure 192 to the controller module housing 101 via the electrical cable 193 allows the user to easily manipulate the electrode support structure 192 to place the exposed ends of the dry electrolyte electrodes in contact with the skin of the neck in the target area. The electrical cable 193 can be, for example, an auxiliary cable of the type typically used as headphone jacks.

With reference to FIG. 21, the electrode support structure 192 comprises an electrical coupling unit 194 and a removable electrode holder 195. In accordance with this representative embodiment, the removable electrode holder 195 plugs into the electrical coupling unit 194 with an auxiliary jack 196 that mates with an auxiliary connector (not shown) inside of the electrical coupling unit 194.

FIG. 23 shows a fully exploded front perspective view of the nerve stimulation device 230 in accordance with another representative embodiment. The nerve stimulation device 230 shown in FIG. 23 is identical to the nerve stimulation device 190 shown in FIGS. 19-21 except that the electrical coupling unit 194 of the electrode support structure 192 shown in FIG. 21 has been eliminated. In accordance with this embodiment, the removable electrode holder 195 of the electrode support structure 192 couples directly to the controller module housing 101 such that the auxiliary jack 196 mates with an auxiliary connector (not shown) inside of the controller module housing 101. This embodiment obviates the need for the electrical cable 193 shown in FIG. 21.

FIGS. 24 and 25 show, respectively, front and right side perspective views of a headset 240 including the electrode support structure of the nerve stimulation device in accordance with another representative embodiment. In accordance with this representative embodiment, the controller (not shown) and the electrical waveform generator (not shown) of the nerve stimulation device are incorporated into the headset 240. The headset 240 is adapted to fit snugly on a head of the subject when the headset 240 is properly worn by the subject. A first headphone 241 of the headset 240 is mechanically coupled to a first end of a band 242 of the headset 240. A second headphone 243 of the headset 240 is mechanically coupled to a second end of the band 242. A first electrode holder 244 of the headset 240 is adapted to hold a first dry electrolyte electrode 245. A second electrode holder 246 of the headset 240 is adapted to hold a second dry electrolyte electrode 247. Electrical wiring (not shown) of the headset 240 extends through the band 242 for electrically coupling the first and second dry electrolyte electrodes 245 and 247, respectively, to the output terminal of the electrical waveform generator, which can be housed along with the controller (not shown) in, for example, the first headphone 241.

Figure 26:
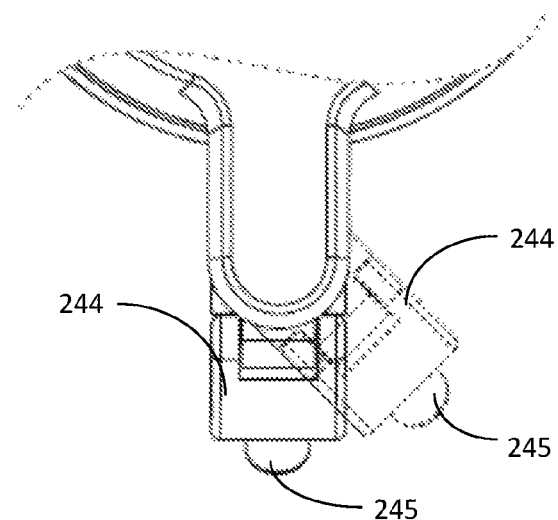
FIG. 26 is a portion of the right side perspective view shown inside of the dashed box labeled 250 in FIG. 25 slightly enlarged to better show the adjustability of one of the electrode holders of the nerve stimulation device.
Figure 27:
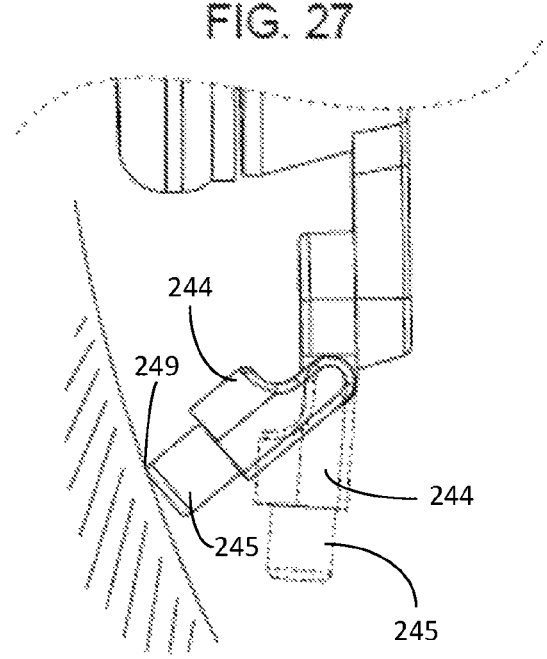
FIG. 27 is a side view of the portion of the right side perspective view shown inside of the dashed box labeled 250 in FIG. 25 slightly enlarged to better show the adjustability of the dry electrolyte electrodes of the nerve stimulation device.

In accordance with a representative embodiment, the first and second electrode holders 244 and 245 are adjustable to allow the subject to position the first ends of the first and second dry electrolyte electrodes 245 and 247, respectively, on the first and second target areas, respectively. FIGS. 26 and 27 show right side and back views of a portion of the view shown inside of the dashed box labeled 250 in FIG. 25 slightly enlarged to better show the adjustability of one of the electrode holders 244 of the nerve stimulation device 240. In FIG. 27, the electrode holder 244 has been adjusted by the user to place the exposed end of the dry electrolyte electrode 245 in contact with the user's neck 249 in the target area.

FIG. 28 shows a front perspective view of a headset 280 including the electrode support structure of the nerve stimulation device in accordance with another representative embodiment. In accordance with this representative embodiment, the controller (not shown) and the electrical waveform generator (not shown) are housed in the controller module housing 101, which is external to the headset 280 and connected to the headset 280 via the electrical cable 193. In all other respects, the headset 280 can be identical to the headset 240 shown in FIG. 24.

FIG. 29 shows front perspective views of the first electrode holder 244 shown in FIGS. 24 and 28 in accordance with a representative embodiment with the dry electrolyte electrode 245 held in the receptacle 291 of the holder 244 and with the dry electrolyte electrode 245 outside of and aligned with the receptacle 291 immediately before or after insertion. The second electrode holder 246 is identical to the first electrode holder 244. In accordance with this representative embodiment, the first and second electrode holders 244 and 246 include an adjustable joint 292 that allows at least one degree of freedom of movement of the holder 244, 245 relative to the headset to allow the exposed end of the dry electrolyte electrodes 245 and 247 to be positioned facing the target area of the neck. Preferably the adjustable joint 291 allows multiple degrees of freedom of movement, including up-and-down movement as well as rotational, pivotal and/or side-to-side movement.

Figure 30:
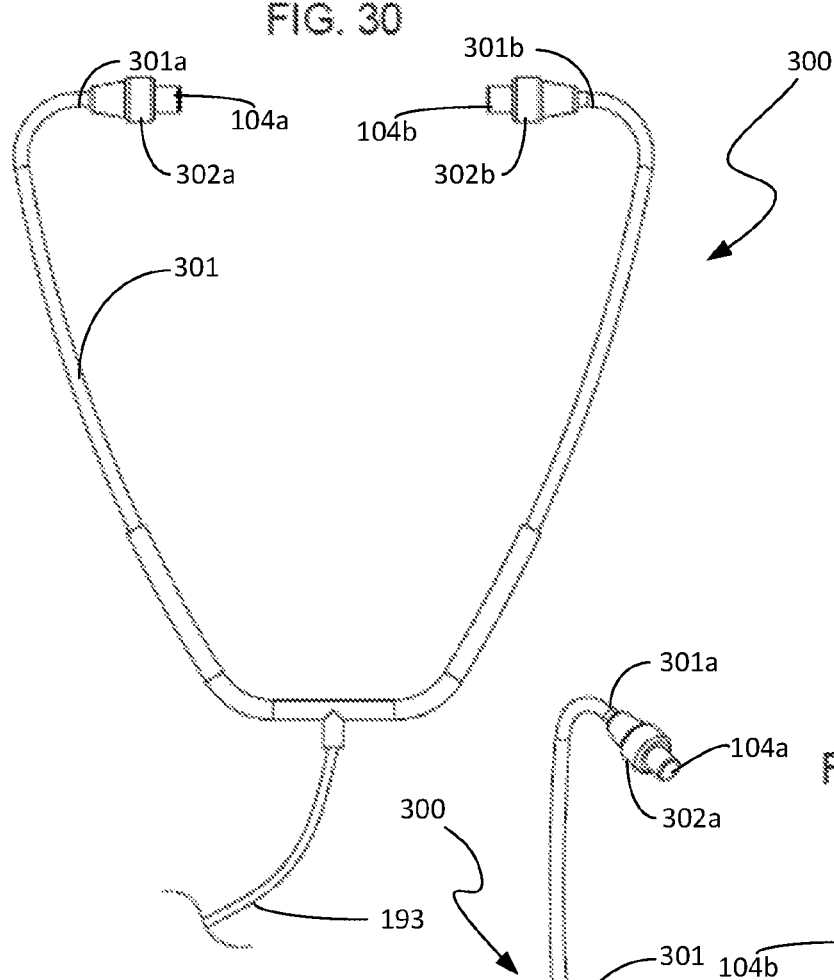
FIGS. 30 and 31 are, respectively, front and side perspective views of a neck attachment including the electrode support structure of the nerve stimulation device in accordance with a representative embodiment.
Figure 31:
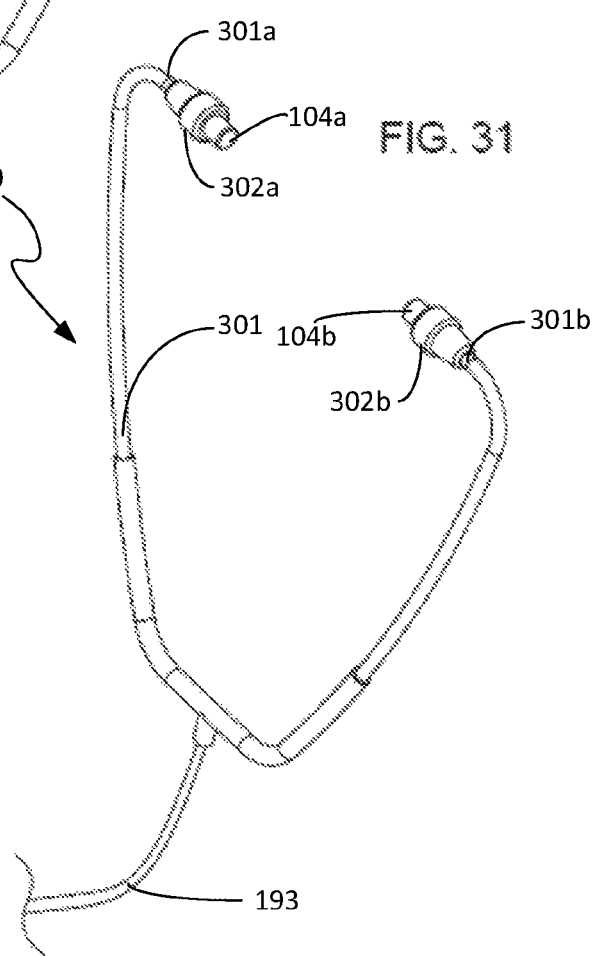
Figure 32:
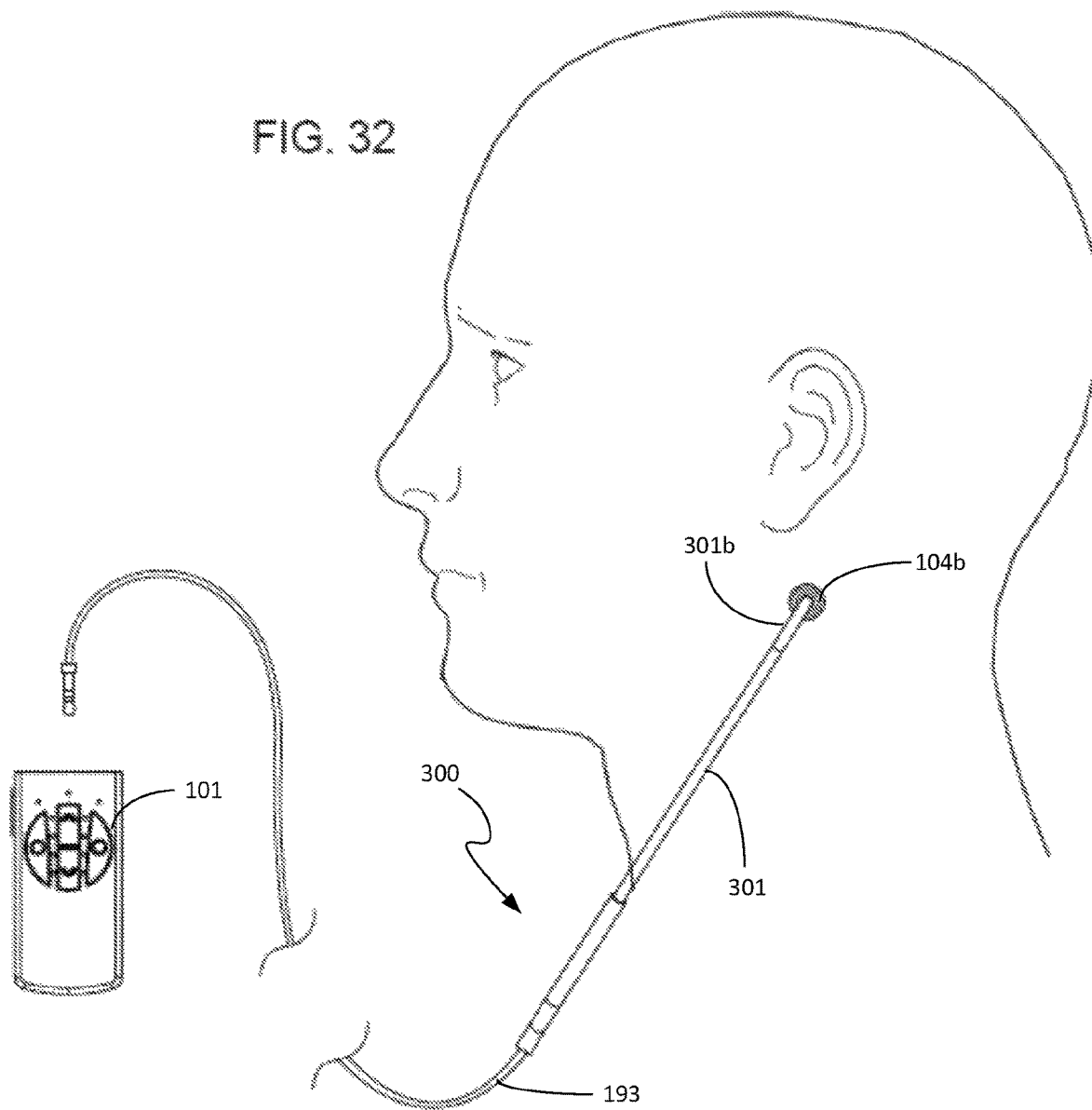
FIG. 32 is a left side perspective view of the neck attachment shown in FIGS. 30 and 31 electrically coupled by an electrical cable to the controller module of the nerve stimulation device and properly placed on a subject.

FIGS. 30 and 31 show, respectively, front and side perspective views of a neck attachment 300 including the electrode support structure of the nerve stimulation device in accordance with another representative embodiment. FIG. 32 shows a left side perspective view of the neck attachment 300 shown in FIGS. 30 and 31 electrically coupled by an electrical cable 193 to the controller module housing 101 of the nerve stimulation device and properly placed on a subject.

The neck attachment 300 comprises a generally U-shaped or V-shaped band 301 adapted to loop below a chin of the subject and first and second ends that are directed inwardly toward first and second target areas of the subject's skin when the neck attachment 300 is properly worn by the subject, as shown in FIG. 32. A first electrode holder 302a disposed on the first end 301a of the band 301 is adapted to hold the first dry electrolyte electrode 104a. A second electrode holder 302b disposed on the second end 301b of the band 301 is adapted to hold the second dry electrolyte electrode 104b. Electrical wiring (not shown) of the neck attachment 300 extends through the band 301 for electrically coupling the first and second dry electrolyte electrodes 104a and 104b, respectively, to the output terminal of the electrical waveform generator, which is contained within the controller module housing 101 in accordance with this representative embodiment.

Figure 33:
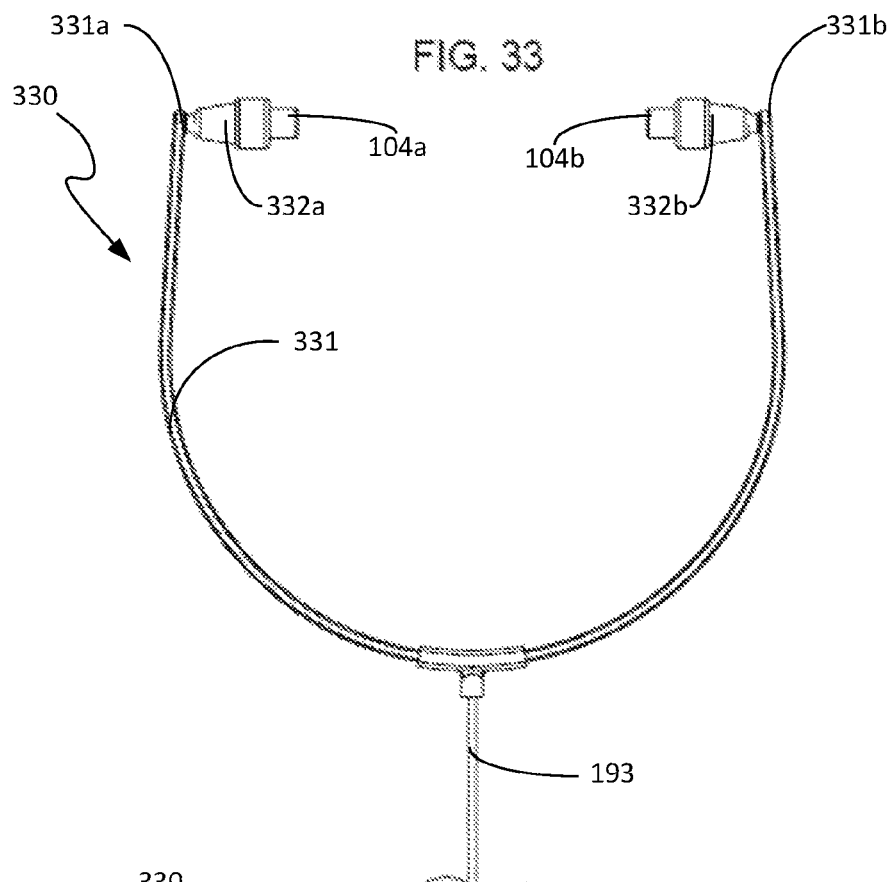
FIGS. 33 and 34 are, respectively, front and top perspective views of a neck attachment including the electrode support structure of the nerve stimulation device in accordance with a representative embodiment.
Figure 34:
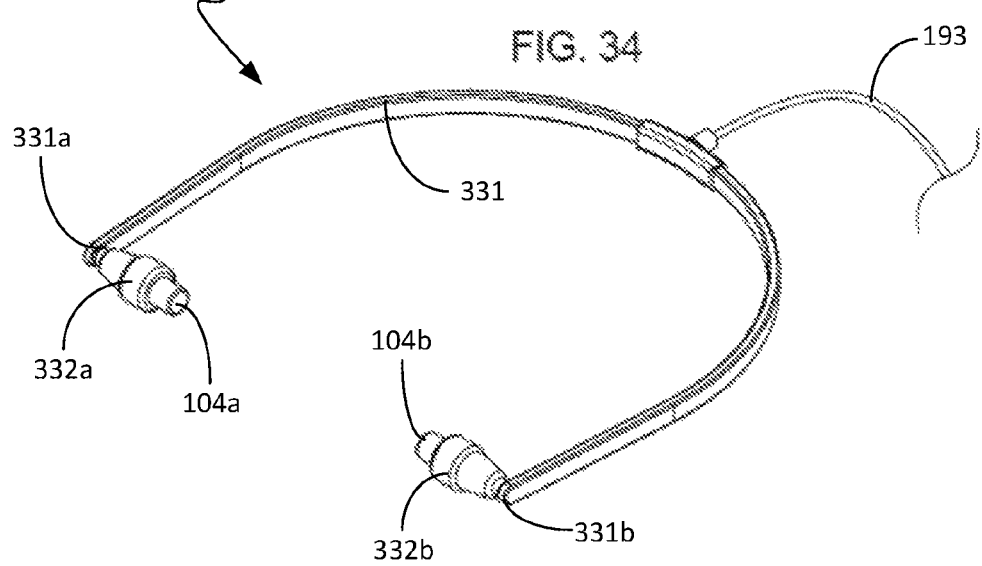
Figure 35:
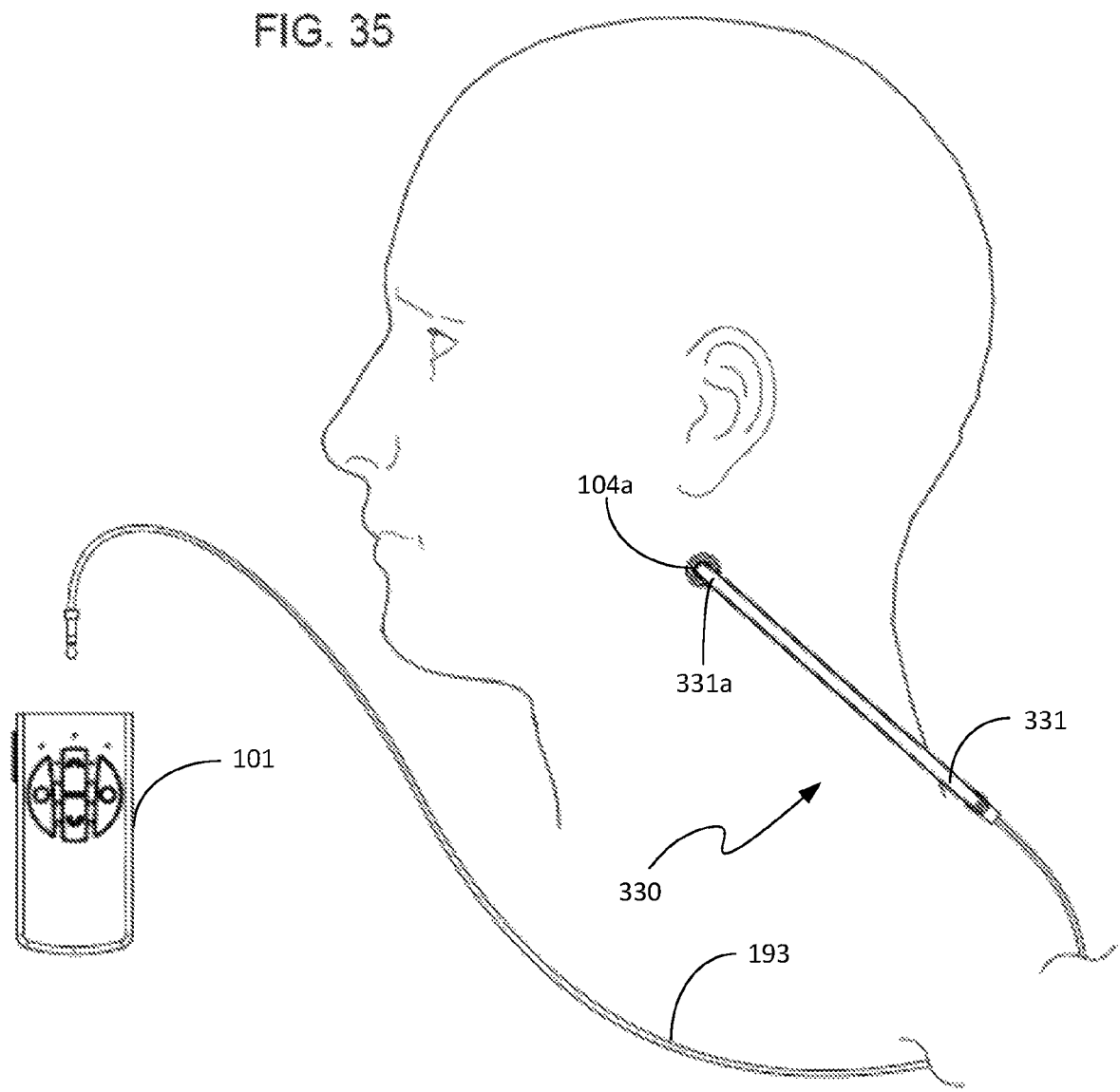
FIG. 35 is a left side perspective view of the neck attachment shown in FIGS. 33 and 34 electrically coupled by an electrical cable to the controller module of the nerve stimulation device and properly placed on a subject.

FIGS. 33 and 34 show, respectively, front and top perspective views of a neck attachment 330 including the electrode support structure of the nerve stimulation device in accordance with a representative embodiment. FIG. 35 shows a left side perspective view of the neck attachment 330 shown in FIGS. 33 and 34 electrically coupled by an electrical cable 193 to the controller module housing 101 of the nerve stimulation device and properly placed on a subject. The neck attachment 300 comprises a generally U-shaped or V-shaped band 331 adapted loop behind the neck of the subject and first and second ends 331a and 331b, respectively, that are adjacent opposite sides of the subject's neck when the neck attachment 330 is properly worn by the subject, as shown in FIG. 35. A first electrode holder 332a disposed on the first end 331a of the band 331 is adapted to hold the first dry electrolyte electrode 104a. A second electrode holder 332b disposed on the second end 331b of the band 331 is adapted to hold the second dry electrolyte electrode 104b. Electrical wiring (not shown) of the neck attachment 330 extends through the band 331 for electrically coupling the first and second dry electrolyte electrodes 104a and 104b, respectively, to the output terminal of the electrical waveform generator, which is contained within the controller module housing 101 (FIG. 35) in accordance with this representative embodiment.

FIG. 36 shows a front perspective view of a neck attachment 360 including the electrode support structure of the nerve stimulation device in accordance with another representative embodiment. FIG. 37 shows a left side perspective view of the neck attachment 360 shown in FIG. 36 properly placed on a subject. The neck attachment 360 is similar to the neck attachment 330 shown in FIGS. 33-35 except that the controller of the nerve stimulation device is a smart phone or a separate wireless-enabled controller 370 and the electrical waveform generator is incorporated along with a wireless receiver or transceiver into a module 380 of the neck attachment 360. The wireless receiver or transceiver of the module 380 communicates wirelessly with the smart phone or wireless-enabled controller 370 via a wireless link to receive and execute commands sent by the smart phone or wireless-enabled controller 370. The wireless receiver or transceiver of the module 380 then interprets the commands and selects the type and amplitude of the waveform to be generated by and output from the output terminal of the waveform generator, which is electrically coupled to the first and second dry electrolyte electrodes 104a and 104b, respectively, by electrical wiring extending through the band 331. In all other respects, the neck attachment 360 can be identical to the neck attachment 330.

FIG. 38 shows a front perspective view of the nerve stimulation device 380 in accordance with another representative embodiment including a controller module housing 101, an electrode support structure 381 and an electrical cable 193 that can be used to electrically connect the electrode support structure 381 to the controller module housing 101. FIG. 39 shows a left side perspective view of the nerve stimulation device 380 shown in FIG. 38 with a removable protective cap 103 positioned above, and in alignment with, the electrode support structure 381; the controller module housing 101 is not shown in FIG. 39 for ease of illustration.

The electrode support structure 381 comprises the removable electrode holder 195 shown earlier in FIG. 21 and an electrical coupling unit 383 that is electrically coupled via electrical cable 193 to the controller module housing 101. The nerve stimulation device 380 is similar to the nerve stimulation device 190 shown in FIG. 19 except that the electrical coupling unit 383 has an exterior that is different from that of the electrical coupling unit 194 of the nerve stimulation device 190. The nerve stimulation device 380 is used in the same manner in which the nerve stimulation device 190 is used, as described above with reference to FIGS. 19-22.

FIG. 40 shows a front perspective view of an upper portion of the nerve stimulation device 380 shown in FIG. 38 with the electrical coupling unit 383 of the electrode support structure 381 shown in FIG. 38 removed to allow the removable electrode holder 195 of the electrode support structure 381 to couple directly with the controller module housing 101, thereby obviating the need for the electrical cable 193 and the electrical coupling unit 383. In accordance with this representative embodiment, the controller module housing 101 has first and second electrical contacts 401a and 401b, respectively, that come into contact with respective electrical contacts (not shown) of the removable electrode holder 195 when the controller module housing 101 and the removable electrode holder 195 are coupled together. These electrical contacts electrically couple the output terminal of the electrical waveform generator with the first and second dry electrolyte electrodes 104a and 104b, respectively. During treatment, the nerve stimulation device shown partially in FIG. 40 is operated in the same manner in which the nerve stimulation device 100 shown in FIG. 1 is operated, as previously described.

FIG. 41 shows a front perspective view of the nerve stimulation device 380 shown in FIG. 38 with the controller module housing 101 and the electrode support structure 381 electrically interconnected via the electrical cable 193. FIG. 42 shows a front perspective view of the removable electrode holder 195 of the electrode support structure 381 shown in FIG. 38. FIG. 43 shows a front perspective view of the electrical coupling unit 383 of the electrode support structure 381 shown in FIG. 38 and an upper portion of the controller module housing being electrically connected via the electrical cable 193. In FIG. 43 it can be seen that the electrical coupling unit 383 has first and second electrical contacts 431a and 431b, respectively, that come into contact with respective electrical contacts (not shown) of the removable electrode holder 195 when the two are coupled together to form the assembled electrode support structure 381 shown in FIG. 41. This design of the nerve stimulation device 380 has great configuration versatility in that the removable electrode holder 195 can be coupled to the electrical coupling unit 383, which is then coupled via the electrical cable 193 to the controller module housing 101, or the removable electrode holder 195 can be coupled directly to the controller module housing 101.

FIG. 44 shows a front perspective exploded view of the nerve stimulation device 440 in accordance with another representative embodiment in which the removable electrode holder 195 couples directly with the controller module housing 101, as described above with reference to FIG. 40. FIG. 45 shows a front perspective view of the nerve stimulation device 440 shown in FIG. 44 with the removable electrode holder 195 coupled directly with the controller module housing 101 and with a removable protective cap 103 positioned above, and aligned with, the removable electrode holder 195. FIG. 46 shows a front perspective view of the nerve stimulation device 440 shown in FIG. 45 with the removable protective cap 103 removably secured to the removable electrode holder.

Figure 3:
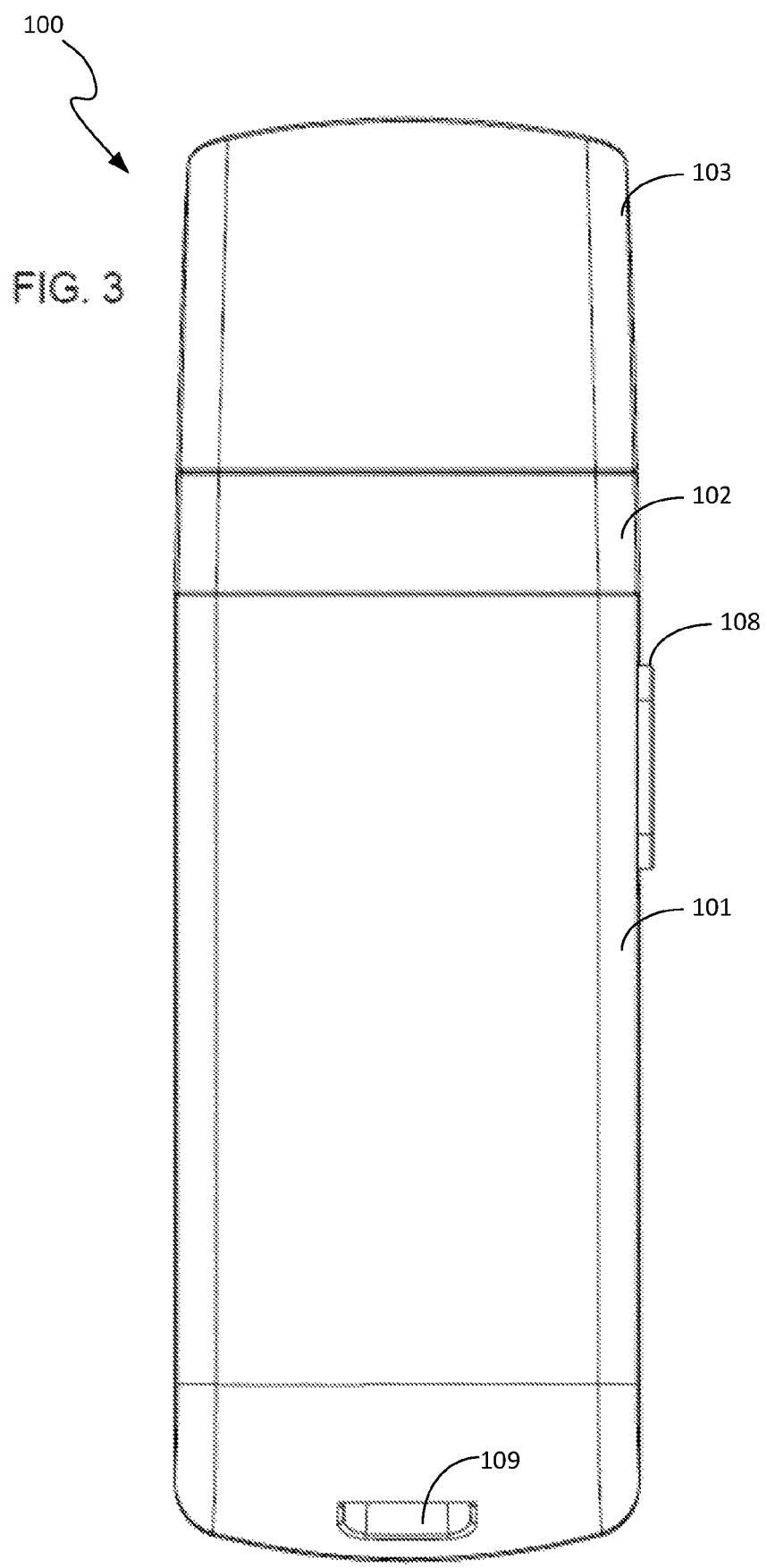
Figure 47:
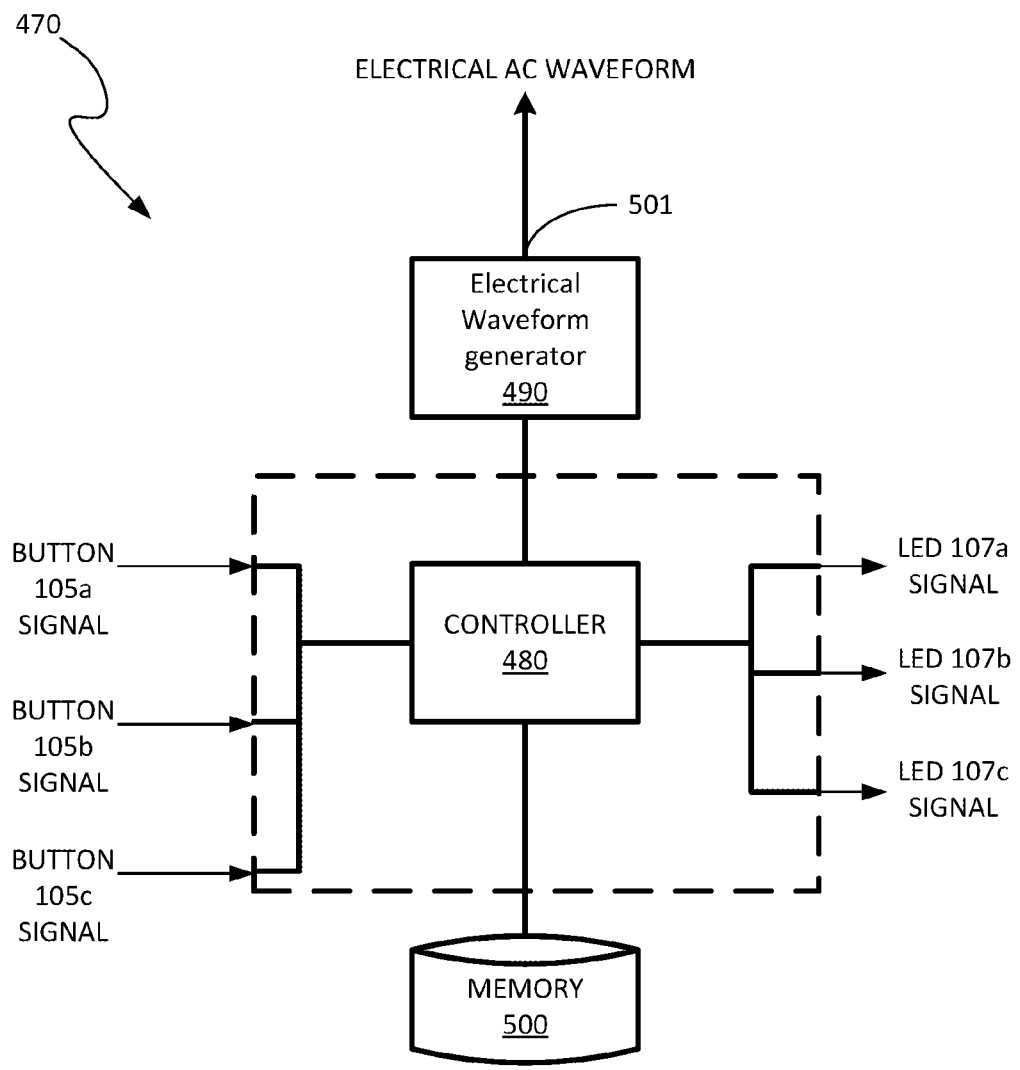
FIG. 47 is a block diagram of the electrical circuitry that can be housed inside of the controller module housing shown in FIGS. 1-5.

FIG. 47 is a block diagram of the electrical circuitry 470 of the nerve stimulation device in accordance with a representative embodiment. The electrical circuitry 470 comprises the aforementioned controller 480, the aforementioned electrical waveform generator 490, a memory device 500, and a power source 401 that preferably is rechargeable via the UBS port 109 (FIG. 3). The controller 480 and the electrical waveform generator 490 can be housed in the same housing, such as the controller module housing 101, or they can be housed separately with a communication link between them (e.g., the controller 480 can be a controller or processor of a smart phone and the electrical waveform generator 490 can be housed in a module 380 of a headset (FIG. 37)).

The controller 480 processes signals corresponding to the buttons 105a-105c being pressed by the user to cause the electrical waveform generator 490 to generate the selected waveform having the selected amplitude, as previously described. The dry electrolyte electrodes 104a, 104b or 134a, 134b are electrically coupled in the manner described above to the output terminal 501 of the electrical waveform generator 490. For whichever of the waveforms is selected by the controller 480 based on the signals from buttons 105a-105c, the controller 480 sends signals to the LEDs 107a-107c to cause them to either be turned on or turned off, as mentioned previously. The memory device 500 typically stores data and computer instructions for execution by the controller 480. The computer instructions correspond to computer algorithms that are performed by the controller 480 to cause it to perform the aforementioned tasks. The memory device 500 is a non-transitory computer readable medium.

Methods of Using the Nerve Stimulation Device

With reference again to FIG. 1, to use the nerve stimulation device 100, the user, which can be the subject to be treated, grips the controller module housing 101 in the fingers of one hand and moves the nerve stimulation device 100 to place the exposed ends of the dry electrolyte electrodes 104a and 104b, or 134a and 134b, against the skin of the neck in the target area. The user moves the switch 108 to the on position and uses the buttons 106a-106c to select a waveform to be applied and the amplitude of the waveform. The user can change these settings as desired during use to improve treatment conditions.

In various aspects, methods of using the nerve stimulation devices are provided. The methods can include non-invasive nerve stimulation of one or both of the treat auricular nerve and the auricular branch of the vagus nerve through a target nerve junction containing the great auricular nerve and the auricular branch of the vagus nerve in a neck of a subject in need thereof. In some aspects, the subject is suffering from a psychiatric disorder such as a fear and/or anxiety disorder, an addictive disorder, or a mood disorder. In some aspects, the disorder is an anxiety disorder. Anxiety disorders can include a panic disorder, a phobia, post-traumatic stress disorder (PTSD), social anxiety disorder, or obsessive-compulsive disorder (OCD). In some aspects, the methods can treat or alleviate the disorder in the subject. The treating can include lower, reducing, or alleviating one or more symptoms of the disorder in the subject.

The term "subject" as used herein refers to vertebrate or invertebrate, including a mammal. The term "subject" includes human, animal, a bird, a fish, or an amphibian. Typical, non-limiting examples of a "subject" include humans, cats, dogs, horses, sheep, bovine cows, pigs, lambs, rats, mice and guinea pigs.

The terms "lower", "reduced", "reduction" or "decrease" or "inhibit" are all used herein generally to mean a decrease by a statistically significant amount. However, for avoidance of doubt, "lower", "reduced", "reduction" or "decrease" or "inhibit" means a measurable, observable, or detectable decrease, such as a decrease by at least 5%, 10%, 15%, 20%, 25%, 30%, 35%, 40%, 45%, 50%, 55%, 60%, 65%, 70%, 75%, 80%, 85%, 90%, or 95%. In some embodiments, a decrease by at least 10% as compared to a reference level, for example a decrease by at least about 20%, or at least about 30%, or at least about 40%, or at least about 50%, or at least about 60%, or at least about 70%, or at least about 80%), or at least about 90% or up to and including a 100%) decrease (i.e. absent level as compared to a reference sample), or any decrease between 10-100%) as compared to a reference level.

Reference to treating and preventing a psychiatric disorder such as a fear and/or anxiety disorder, an addictive disorder, or a mood disorder, as used herein includes, inter alia, the inhibition or alleviation, at least in part, of one or more symptoms of the psychiatric disorder. By way of example, symptoms of depression, anxiety and related disorders that may be inhibited or alleviated include irritability, mood swings, depressed mood, disturbed sleep, listlessness, short term memory loss, anxiousness, restlessness, tension, poor self-esteem, suicidal thoughts or suicidal tendencies. Further, "treating or preventing" includes preventing the development of depression, anxiety or a depressive or anxiety-related disorder in a subject that may be predisposed to such a condition or may display one or more symptoms of such a condition but has not yet been diagnosed with the condition. "Treating or preventing" also include preventing the onset of a depressive episode or anxiety episode in a subject.

Though anxiety and anxious feelings are common, an anxiety disorder is typically diagnosed only when the symptoms reach a threshold and last at least two weeks. There exist a number of methods and techniques well known to those skilled in the art for diagnosing depression, anxiety and depressive or anxiety-related disorders, for assessing the status or severity of such conditions or symptoms thereof over time, and for monitoring the change in status or severity of such conditions or symptoms thereof over time, including in response to treatment or therapy.

Such methods and techniques for diagnosing, assessing and monitoring anxiety and anxiety-related disorders may include clinician assessment, self-assessment or self-reporting questionnaires, and clinician-completed reports or questionnaires, in addition to biochemical measurements. A variety of clinical measures of symptoms and mood are well known to those skilled in the art. The present disclosure contemplates the use of any such method(s) or technique(s) in diagnosing anxiety or a anxiety-related disorder and for assessing or monitoring such conditions as part of, for example, an initial determination of the suitability of an individual to be treated in accordance with the present disclosure or a determination of the efficacy of a treatment in accordance with the present disclosure in an individual. In some aspects, the methods include the State-Trait Anxiety Inventory (STAI; Spielberger et al. (1970) Manual for the State-Trait Anxiety Inventory (self-evaluation questionnaire) (Consulting Psychologists Press, Palo Alto, Calif.)), which is comprised of 40 items divided evenly between state anxiety and trait anxiety. In some aspects, the methods can result Ina decreased anxiety in the subject when measured using the STAI.

Other examples of self-assessment or self-report questionnaires include, but are not limited to the Depression and Anxiety Stress Scale (DASS), the Outcome Quiestionnaire-45 (OQ45), Quality of Life in Depression Scale (QLDS, including a Quality of Life (QoL) score), the Beck Depression Inventory (BDI), the Warwick-Edinburgh Mental Well-Being Scale (WBS), the Mini International Neuropsychiatric Interview (MINI), the Structured Clinical Interview for DSM Disorders (SCID) and the Patient Health Questionnaire (PHQ, such as PHQ-9 and PHQ-2). Exemplary clinician-completed reports or questionnaires include, but are not limited to, the Hamilton Depression Rating Scale (HAM-D) and the Raskin Depression rating Scale. Biochemical measurements that may be employed include, but are not limited to, whole blood serotonin levels.

It should be noted that the nerve stimulation device and methods of use have been described above with reference to various representative, or exemplary, embodiments for the purpose of describing inventive principles and concepts, and that the inventive principles and concepts are not limited to the embodiments described above. For example, the nerve stimulation devices are shown in the drawings as having particular shapes and features, but they can have other shapes and features not explicitly described herein. For example, the nerve stimulation device is not limited to having the particular user interface shown in FIG. 1 for selecting the waveform and its amplitude, or for indicating which waveform has been selected. Also, the nerve stimulation device is not limited to having any particular shapes. The handheld, headset and neck attachment designs are examples of suitable designs, but the inventive principles and concepts are not limited to these designs, as will be understood by those of skill in the art in view of the present disclosure. It will be understood by those skilled in the art in view of the description provided herein that the inventive principles and concepts are not limited to these embodiments or examples. Many modifications can be made to the systems and methods described herein within the scope of the inventive principles and concepts, as will be understood by those of skill in the art.

What is claimed is:

1. A nerve stimulation device for non-invasive nerve stimulation of one or both of the great auricular nerve and the auricular branch of the vagus nerve in a neck of a subject in need thereof, the nerve stimulation device comprising:
   (i) a controller;
   (ii) an electrical waveform generator in communication with and controlled by the controller, the electrical waveform generator being configured to output an alternating current (AC) waveform from an output terminal of the electrical waveform generator;
   (iii) an electrode support structure; and
   (iv) at least first and second dry electrolyte electrodes coupled to the electrode support structure and electrically coupled to the output terminal of the electrical waveform generator;
   wherein each of the first and second dry electrolyte electrodes comprise:
      (a) an electrically-conductive material,
      (b) a first end that is adapted to be placed in contact with a skin in the neck of the subject at a target nerve junction containing the great auricular nerve and the auricular branch of the vagus nerve, and
      (c) a second end opposite the first end, the second end adapted to be electrically coupled to the output terminal;
   wherein a length of each dry electrolyte electrode defined as a distance between the first end and the second end of each dry electrolyte electrode is such that, when the stimulation device is in use, the stimulation device stimulates the great auricular nerve or the auricular branch of the vagus nerve of the subject while minimizing the occurrence of hot spots between the skin and the first end of the dry electrolyte electrode,
   wherein the electrode support structure comprises (i) a first electrode receptacle for receiving the second end of the first dry electrolyte electrode and (ii) a second electrode receptacle for receiving the second end of the second dry electrolyte electrode.

2. The nerve stimulation device according to claim 1, wherein the first dry electrolyte electrode is secured in the first electrode receptacle and the second dry electrolyte electrode is secured in the second electrode receptacle by friction.

3. The nerve stimulation device according to claim 2, wherein the electrode support structure comprises a two-part electrode support structure comprising (i) a first electrode support structure comprising the first electrode receptacle and (ii) a second electrode support structure comprising the second electrode receptacle.

4. The nerve stimulation device according to claim 2, wherein the electrode support structure comprises a skin-contacting surface comprising the first electrode receptacle and the second electrode receptacle;
   wherein the skin-contacting surface is at an angle with respect to a long axis of one or both of the first dry electrolyte electrode and the second dry electrolyte electrode when the dry electrolyte electrodes are in the electrode receptacles.

5. The nerve stimulation device according to claim 4, wherein the angle is about 30° to about 75°.

6. The nerve stimulation device according to claim 4, wherein the skin-contacting surface comprises a curved surface.

7. The nerve stimulation device according to claim 4, wherein the first end of each of the dry electrolyte electrodes extend above the skin-contacting surface when the dry electrolyte electrodes are secured in the receptacles.

8. A nerve stimulation device for non-invasive stimulation of one or both of the great auricular nerve and the auricular branch of the vagus nerve in a neck of a subject in need thereof, the nerve stimulation device comprising:
   a controller;
   a waveform generator coupled with the controller, the waveform generator configured to controllably generate an alternating current (AC) waveform; and
   at least first and second dry electrolyte electrodes coupled with the waveform generator; wherein each of the first and the second dry electrolyte electrodes have a length defined as a distance between a first end and a second end opposite the first end, the first end adapted to be placed in contact with a skin in the neck of the subject at a target nerve junction containing the great auricular nerve and the auricular branch of the vagus nerve, such that when the nerve stimulation device is in use, the nerve stimulation device stimulates the great auricular nerve or the auricular branch of the vagus nerve of the subject while minimizing the occurrence of hot spots between the skin and the first end of the dry electrolyte electrode.

9. The nerve stimulation device according to claim 8, wherein the volume of each dry electrolyte electrode is about 0.1 cubic centimeter ($cm^3$) to less than 50 $cm^3$ or about 2 cm to about 20 cm.

10. The nerve stimulation device according to claim 8, wherein one or both of the first dry electrolyte electrode and the second dry electrolyte electrode comprise a polymer hydrogel that is doped with an electrolyte.

11. The nerve stimulation device according to claim 8, wherein each of the first and second dry electrolyte electrodes has a length measured from an outer circumference of the respective first end to a respective second end opposite the respective first end that is preselected to be sufficiently large to ensure, when the nerve stimulation device is in use, that a distribution of electrical current density over an electrically-conductive material of each of the first and the second dry electrolyte electrode is sufficiently high to reduce an occurrence of hot spots at an interface between the first end and the skin of the subject.

12. The nerve stimulation device according to claim 8, further comprising:
a headset including a first headphone, a second headphone, a first electrode holder for holding the first dry electrolyte electrode and a second electrode holder for holding the second dry electrolyte electrode, wherein the controller is incorporated into a smart phone to control the waveform generator, and wherein the nerve stimulation device further comprises:
a wireless receiver in communication with the controller via a wireless link between the wireless receiver and the smart phone or separate wireless-enabled controller, the wireless receiver being in communication with the waveform generator to enable the controller to control the waveform generator, and wherein the wireless receiver and the waveform generator are incorporated into the headset.

13. The nerve stimulation device according to claim 8, further comprising:
a controller module housing that houses the controller and the waveform generator;
an electrode support structure including an electrical coupling unit and a removable electrode holder removably coupled with the electrical coupling unit, the first and second dry electrolyte electrodes being removably secured to the removable electrode holder, the electrical coupling unit comprising an electrical interface between the first and second dry electrolyte electrodes and an output terminal of the electrical waveform generator.

14. The nerve stimulation device of claim 13, further comprising: an electrical cable electrically connected on first and second ends thereof to the electrical coupling unit and to the controller module housing, respectively, to thereby electrically couple the first and second dry electrodes to the output terminal of the electrical waveform generator.

15. The nerve stimulation device of claim 14, further comprising:
a removable cap that is removably secured to the removable electrode holder, wherein while the removable cap is secured to the removable electrode holder, the removable cap covers the first and second dry electrolyte electrodes to protect the first and second dry electrodes from an environment in which the nerve stimulation device is disposed.

16. The nerve stimulation device of claim 13, wherein the first and second dry electrolyte electrodes are removably secured to the removable electrode holder by inserting the first and second dry electrolyte electrodes into first and second receptacles, respectively, of the removable electrode holder, wherein the first and second receptacles are shaped and sized to receive the first and second dry electrolyte electrodes, respectively, in friction fits.

17. The nerve stimulation device of claim 16, wherein the first and second receptacles have first and second axes, respectively, that are generally coaxial with first and second axes of the first and second dry electrolyte electrodes, respectively, when the first and second dry electrolyte electrodes are held in the first and second receptacles, respectively, and wherein the first and second axes of the first and second receptacles are spaced apart from one another by a preselected distance that ranges from 0.1 cm to 50.0 cm.

18. The nerve stimulation device of claim 13, wherein the electrical coupling unit has an interface that is adapted to mate with an interface on the controller module housing, and wherein mating of the interface of the electrical coupling unit with the interface of the controller module housing establishes the electrical coupling of the first and second dry electrolyte electrodes with the output terminal of the electrical waveform generator.

19. The nerve stimulation device according to claim 8, further comprising:
a neck attachment comprising a generally Li-shaped or V-shaped band adapted to loop below a chin of the subject and first and second ends that are directed inwardly toward first and second target areas of the subject's skin when the neck attachment is properly worn by the subject,
a first electrode holder holding the first dry electrolyte electrode,
a second electrode holder holding the second dry electrolyte electrode, and electrical wiring extending through the generally Li-shaped or V-shaped band, and
electrically coupling the waveform generator to the first and the second dry electrolyte electrodes.

20. The nerve stimulation device according to claim 19, wherein the controller and the waveform generator are incorporated in the neck attachment.

21. The nerve stimulation device according to claim 19, wherein the controller is incorporated into a smart phone or separate wireless-enabled controller, and wherein the nerve stimulation device further comprises:
a wireless receiver in communication with the controller via a wireless link between the wireless receiver and the smart phone or separate wireless-enabled controller, the wireless receiver being in communication with the waveform generator to enable the controller to control the waveform generator, and wherein the wireless receiver and the waveform generator are incorporated into the neck attachment.

22. The nerve stimulation device according to claim 8, further comprising:
a neck attachment comprising a generally Li-shaped or V-shaped band adapted to loop behind a neck of the subject and first and second ends that are adjacent opposite sides of the subject's neck when the neck attachment is properly worn by the subject,
a first electrode holder holding the first dry electrolyte electrode,
a second electrode holder holding the second dry electrolyte electrode, and
electrical wiring extending through the generally Li-shaped or V-shaped band and electrically coupling the waveform generator to the first and the second dry electrolyte electrodes.

23. The nerve stimulation device according to claim 22, wherein the controller and the waveform generator are incorporated in the neck attachment.

24. The nerve stimulation device according to claim 22, wherein the controller is incorporated into a smart phone or separate wireless-enabled controller, and wherein the nerve stimulation device further comprises:
a wireless receiver in communication with the controller via a wireless link between the wireless receiver and the smart phone or separate wireless-enabled controller, the wireless receiver being in communication with the waveform generator to enable the controller to control the waveform generator, and wherein the wireless receiver and the waveform generator are incorporated into the neck attachment.

* * * * *